US009386962B2

(12) United States Patent
Dahl et al.

(10) Patent No.: US 9,386,962 B2
(45) Date of Patent: Jul. 12, 2016

(54) METHOD AND APPARATUS FOR EVALUATING OSTEOINTEGRATION OF MEDICAL IMPLANTS

(75) Inventors: Michael C. Dahl, Eden Prairie, MN (US); Randal P. Ching, Bellevue, WA (US)

(73) Assignee: University of Washington, Seattle, WA (US)

( * ) Notice: Subject to any disclaimer, the term of this patent is extended or adjusted under 35 U.S.C. 154(b) by 1130 days.

(21) Appl. No.: 12/427,575

(22) Filed: Apr. 21, 2009

(65) Prior Publication Data

US 2009/0264754 A1    Oct. 22, 2009

Related U.S. Application Data

(60) Provisional application No. 61/046,681, filed on Apr. 21, 2008.

(51) Int. Cl.
*A61B 8/00* (2006.01)
*A61B 8/08* (2006.01)
*A61B 5/00* (2006.01)

(52) U.S. Cl.
CPC .............. *A61B 8/0875* (2013.01); *A61B 8/44* (2013.01); *A61B 5/4504* (2013.01)

(58) Field of Classification Search
CPC .................................................. A61B 8/0875
USPC .................. 73/627, 658; 318/139; 340/870.3; 356/489; 381/312; 433/174; 600/25, 600/349, 437, 438, 439, 443, 472, 449, 587, 600/595; 623/10, 23.5
See application file for complete search history.

(56) References Cited

U.S. PATENT DOCUMENTS 5,024,239 A * 6/1991 Rosenstein .................... 600/587
5,106,361 A * 4/1992 Liboff et al. ..................... 600/13
(Continued)

FOREIGN PATENT DOCUMENTS

CA   WO2008019489   *   2/2008 ............. A61C 19/04

OTHER PUBLICATIONS

L DM Nokes, The use of low-frequency vibration measurement in orthopaedics, IMechE 1999.*
(Continued)

*Primary Examiner* — Amanda Lauritzen Moher
*Assistant Examiner* — Serkan Akar
(74) *Attorney, Agent, or Firm* — Kilpatrick Townsend and Stockton LLP

(57) ABSTRACT

Ultrasound vibrometry is employed to determine the amount of bony in-growth (i.e., osteointegration) into a surgically implanted prosthetic component (or conversely, the degree of implant looseness). While specifically developed for assessing osteointegration for total ankle replacements, the technique has broader application to any joint arthroplasty device. With respect to ankle arthroplasty, a vibration is induced in a patient's ankle in a range of frequencies. A Doppler ultrasound unit scans the ankle, with an imaging plane focused on an implant surface. The vibrations input into the ankle are sinusoidal frequencies, in a range from 80-500 Hz. At a frequency determined to best facilitate vibration of the ankle (e.g., a resonant frequency), the output signal from the Doppler ultrasound is Fourier transformed so that the frequency components of the output signal can be observed. These output Fourier signatures have been shown to correspond to a graded response of implant osteointegration (or looseness).

23 Claims, 21 Drawing Sheets

(56) References Cited

U.S. PATENT DOCUMENTS

| | | | |
|---|---|---|---|
| 5,195,532 A * | 3/1993 | Schumacher et al. | 600/552 |
| 5,368,044 A * | 11/1994 | Cain et al. | 600/552 |
| 5,392,779 A * | 2/1995 | Meredith et al. | 600/437 |
| 5,610,966 A * | 3/1997 | Martell et al. | 378/58 |
| 5,895,357 A * | 4/1999 | Ohtomo | 600/449 |
| 5,938,610 A * | 8/1999 | Ohtomo | 600/449 |
| 5,954,504 A * | 9/1999 | Misch et al. | 433/174 |
| 6,068,597 A * | 5/2000 | Lin | 600/443 |
| 6,095,979 A * | 8/2000 | Ohtomo | 600/449 |
| 6,271,924 B1 * | 8/2001 | Ngoi et al. | 356/489 |
| 6,432,057 B1 * | 8/2002 | Mazess et al. | 600/449 |
| 6,641,537 B2 * | 11/2003 | Morris et al. | 600/449 |
| 6,712,778 B1 * | 3/2004 | Jeffcoat et al. | 600/590 |
| 6,918,763 B2 * | 7/2005 | Huang et al. | 433/72 |
| 7,022,076 B1 * | 4/2006 | Kantorovich et al. | 600/449 |
| 7,241,732 B2 * | 7/2007 | Puzas | 514/16.6 |
| 7,285,091 B2 * | 10/2007 | Blodgett et al. | 600/600 |
| 7,289,639 B2 * | 10/2007 | Abel et al. | 381/312 |
| 7,335,169 B2 * | 2/2008 | Thompson et al. | 601/2 |
| 7,435,232 B2 * | 10/2008 | Liebschner | 600/587 |
| 7,668,667 B2 * | 2/2010 | Robb et al. | 702/35 |
| 7,819,013 B2 * | 10/2010 | Chan et al. | 73/658 |
| 7,918,796 B2 * | 4/2011 | Nycz et al. | 600/439 |
| 2002/0026091 A1 * | 2/2002 | Leysieffer | 600/25 |
| 2004/0077949 A1 * | 4/2004 | Blofgett et al. | 600/472 |
| 2004/0116823 A1 * | 6/2004 | Earthman et al. | 600/552 |
| 2005/0070797 A1 * | 3/2005 | Cadossi et al. | 600/438 |
| 2005/0209535 A1 * | 9/2005 | Dariush | 600/595 |
| 2005/0210983 A1 * | 9/2005 | Klein et al. | 73/627 |
| 2005/0215764 A1 * | 9/2005 | Tuszynski et al. | 530/358 |
| 2005/0249667 A1 * | 11/2005 | Tuszynski et al. | 424/9.3 |
| 2006/0025648 A1 * | 2/2006 | Lupin et al. | 600/25 |
| 2007/0085496 A1 * | 4/2007 | Philipp et al. | 318/139 |
| 2007/0106138 A1 * | 5/2007 | Beiski et al. | 600/349 |
| 2007/0238992 A1 * | 10/2007 | Donofrio et al. | 600/437 |
| 2008/0119421 A1 * | 5/2008 | Tuszynski et al. | 514/34 |
| 2008/0262347 A1 * | 10/2008 | Batchelder et al. | 600/437 |
| 2009/0131838 A1 * | 5/2009 | Fotiadis et al. | 601/2 |
| 2009/0198334 A1 * | 8/2009 | Kraus | 623/10 |
| 2009/0322557 A1 * | 12/2009 | Robb et al. | 340/870.3 |

OTHER PUBLICATIONS

Marina Storani de Almeida, Carlos Dias Maciel and Josê Carlos Pereira, Proposal for an Ultrasonic Tool to Monitor the Osseointegration of Dental Implants, Sensors 2007, 7, 1224-1237.*

How much can a vibrational diagnostic tool reveal in total hiparthroplasty loosening? Clinical Biomechanics 18 (2003) 444-458, Clinical Biomechanics 18 (2003) 444-458.*

Nadine Conza y, Bram Soethoudt y, Ester Vlaanderen z, Daniel J. Rixen, In vivo Bone Vibration Measurement by Ultrasound, Conference: 2006 IMAC-XXIV: Conference & Exposition on Structural Dynamics.*

A. Rowlands, F.A. Duck, J.L. Cunningham, Bone vibration measurement using ultrasound: Application to detection of hip prosthesis loosening, Medical Engineering & Physics 30 (2008) 278-284.*

Petro Julkunen, Bone Density Measurement Using Ultrasound, Biomedical ultrasound 2, .2005.*

A.P Georgiou, J.L. Cunnigham, Accurate Diagnosis of Hip Prosthesis loosening using vibrational technique, Clinical Biomechanics, 16 (2001) 315-323.*

Backhauset al., Guidelines for musculoskeletal ultrasound in rheumatology, Ann Rheum Dis 2001;60:641-649.*

Schneideret al., "Primary Stability of Cemented and Noncemented Implants", Springer-Verlag Berlin Heidelberg 1995.*

Almeida et al "Proposal for an Ultrasonic Tool to Monitor the Osseointegration of Dental Implants" Sensors 2007, vol. 7, pp. 1224-1237.*

Dahl, Michael Charles, "An Alternative to Disc Fusion: The Dynamic Characteristics of the Bryan Cervical Disc System", Master's thesis, University of Washington, 2003, 72 pages.

Dahl, Michael Charles, "The Efficacy of using Vibrometry to Detect Osseointegration of the Agility Total Ankle", Doctoral dissertation, University of Washington, 2008, 126 pages.

* cited by examiner

METHOD AND APPARATUS FOR EVALUATING OSTEOINTEGRATION OF MEDICAL IMPLANTS

RELATED APPLICATIONS

This application is based on a prior provisional application Ser. No. 61/046,681, filed on Apr. 21, 2008, the benefit of the filing date of which is hereby claimed under 35 U.S.C. §119(e).

BACKGROUND

Joint pathology is a debilitating disease that can have devastating effects on an individual's quality of life and physical well being. The incidence of joint pathology is quite high, with an individual's chance of acquiring joint pathology increasing with age.

Perhaps the most common joint pathology is arthritis, which is the second most common chronic condition in the United States, affecting over 46 million people annually. There are many methods of treating or temporarily alleviating arthritis, although in severe cases the only way to stop pain and regain lost motion is through total joint replacement.

Total joint replacement is thus the standard treatment for serious joint pathology, and over 980,000 joint replacement procedures were performed in the United States in 2005. Hip and knee arthroplasties were first performed in the 1960's, and such arthroplasties are generally 90-98% successful over a 10 year span. However, ankle arthroplasty is typically much less successful.

A prominent weakness of replacement (artificial) ankle joints is the bond between the talar component of the prosthesis and the talus. Early artificial joints were cemented into place. Over time, it was recognized that if certain materials (such as titanium) were used in fabricating the artificial joint, bone would grow around and into the surfaces of the artificial joint components that were in contact with the residual (remaining) bone, increasing the likelihood that the artificial joint would be successful over the long term. This process of bone growth is referred to as osteointegration. Theoretically, osteointegration can provide the required bond between an artificial joint component and the bone. If too much strain (motion) occurs between the artificial joint component and the bone, osteointegration will be unlikely to occur. Artificial ankle joints appear particularly at risk for such failure because their smaller relative size (and resulting contact area) increases the stress at the joint's bone-implant interface when a patient stands or walks. This increase in stress magnitude would in turn produce higher strains, which may subsequently reduce the likelihood of osteointegration.

Conventionally, a complicated weight-bearing rehabilitation protocol is used to allow patients to gradually adjust (increase) the forces applied to a new prosthesis, allowing the bone to take hold. However, osteointegration rates can vary between patients, and such a rehabilitation procedure does not actually measure the degree of osteointegration for a particular patient. Unfortunately, conventional techniques cannot be used to non-invasively determine when sufficient osteointegration has occurred to enable normal stress loads to safely be applied to such artificial ankle joints.

SUMMARY

The disclosures and drawings of each patent application and issued patent identified above as a related application are specifically incorporated herein by reference.

The following discussion discloses a novel method and apparatus to provide quantitative feedback regarding the status of patient implant osteointegration. In an exemplary, but not limiting embodiment, the concepts disclosed herein are used to evaluate a degree of osteointegration of an artificial ankle joint. Significantly, these concepts enable the osteointegration of an artificial joint to be evaluated non-invasively, by inducing vibrations in a patient proximate to the artificial joint, using ultrasound to non-invasively collect data indicative of how the induced vibrations have been modified by the artificial joint, and analyzing the ultrasound data collected to evaluate the degree of osteointegration of the artificial joint.

In an exemplary but not limiting embodiment, the step of analyzing the ultrasound data to evaluate the degree of osteointegration of the artificial joint in the patient involves comparing the ultrasound data to historical ultrasound data that have been calibrated to degrees of osteointegration as measured inter-operatively using laser vibrometry.

In another exemplary but not limiting embodiment, the step of analyzing the ultrasound data to evaluate the degree of osteointegration of the artificial joint in the patient involves comparing the ultrasound data to historical ultrasound data that have been calibrated to degrees of osteointegration as determined by a medical practitioner during an invasive examination of the artificial joint.

The concepts disclosed herein thus encompass clinical quantification of the level of osteointegration for a patient's ankle prosthesis, and inter-operative quantification of the level of osteointegration for a patient's ankle prosthesis. Both the clinical osteointegration quantification and the inter-operative osteointegration quantification employ Doppler laser vibrometry. These techniques predict the level of osteointegration in the talar component based upon the spectrum of the prosthesis-ankle system's vibrational output measured non-invasively using ultrasound, and the spectrum of the prosthesis-ankle system's vibrational output inter-operatively measured using a Doppler laser vibrometer.

Significantly, the clinical quantification can be used non-invasively to evaluate when artificial ankle joints are sufficiently well osteointegrated to accommodate normal stresses without risking failure of the prosthesis. Furthermore, this quantification can also be used in the clinical assessment of whether a patient's post-operative pain may be associated with a loose (poorly integrated) implant, which may thus require an additional surgery.

Related apparatus are characterized as including a vibration generator for non-invasively inducing vibrations in the patient proximate the medical prosthesis; an ultrasound component to non-invasively collect ultrasound data indicative of how the induced vibrations have been modified by the medical prosthesis; and a processor that analyzes the ultrasound data to evaluate the degree of osteointegration of the medical prosthesis in the patient.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1 schematically illustrates an ultrasound probe being used to non-invasively collect data that can be used to evaluate a degree of osteointegration of a medical implant;

Figure 5:
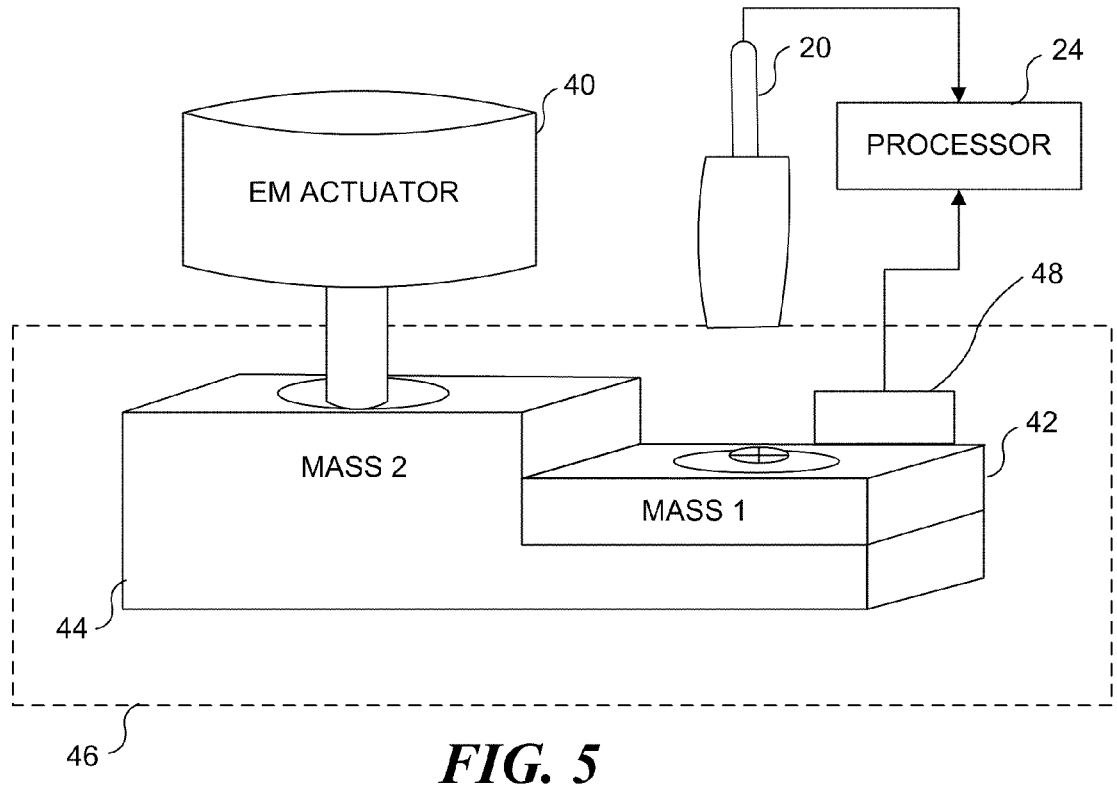
Figure 6:
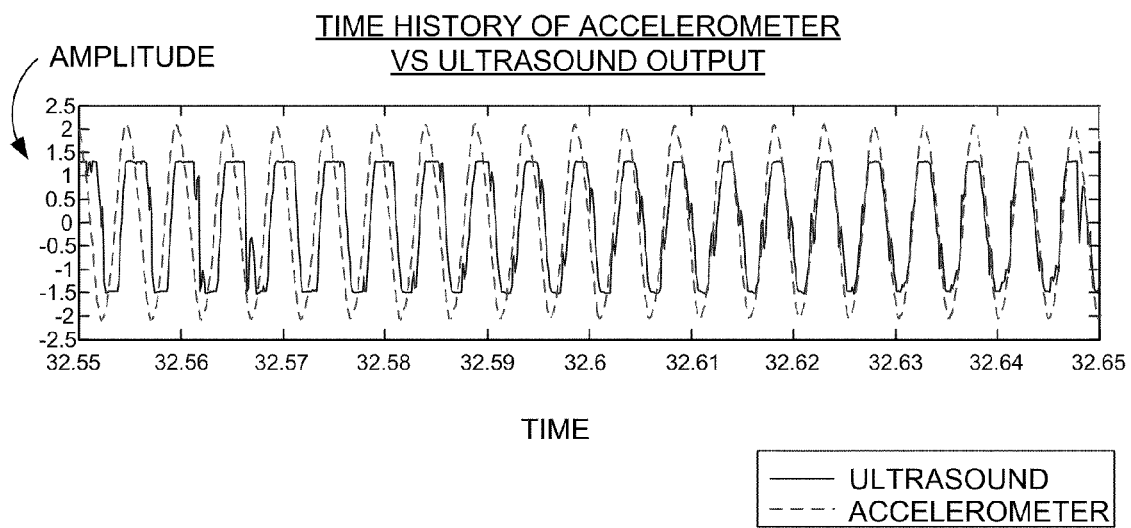
Figure 7A:
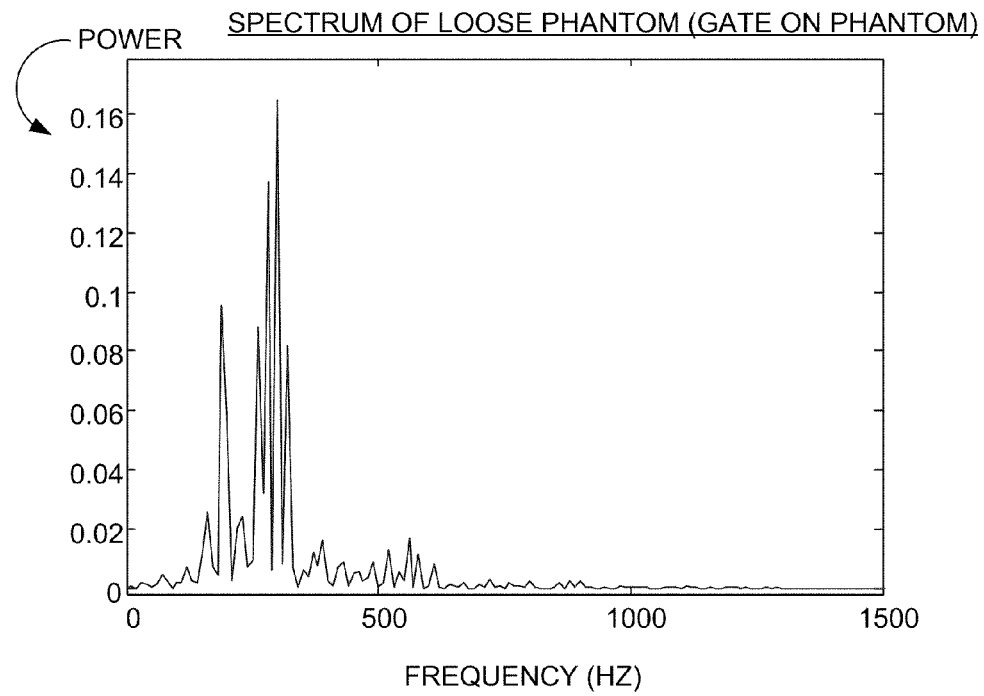
Figure 7B:
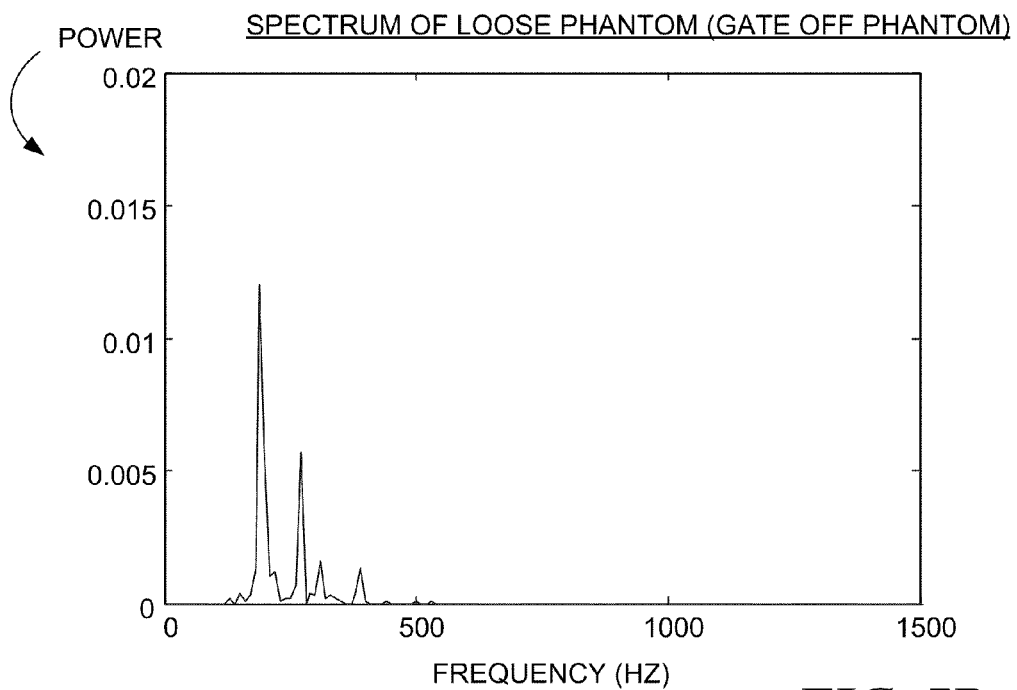
Figure 8:
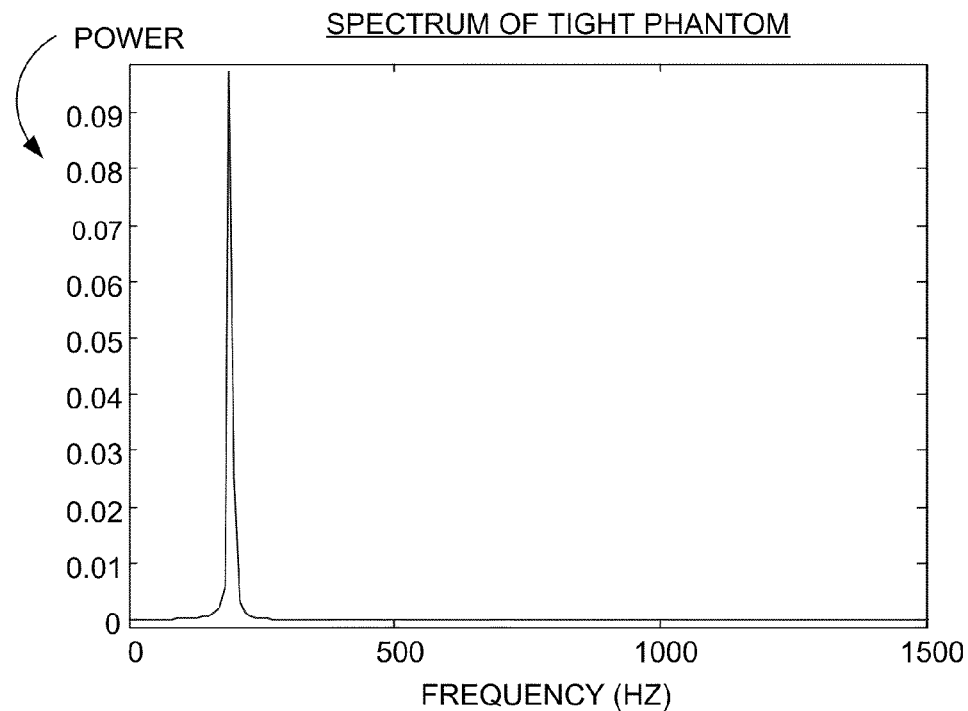
Figure 9:
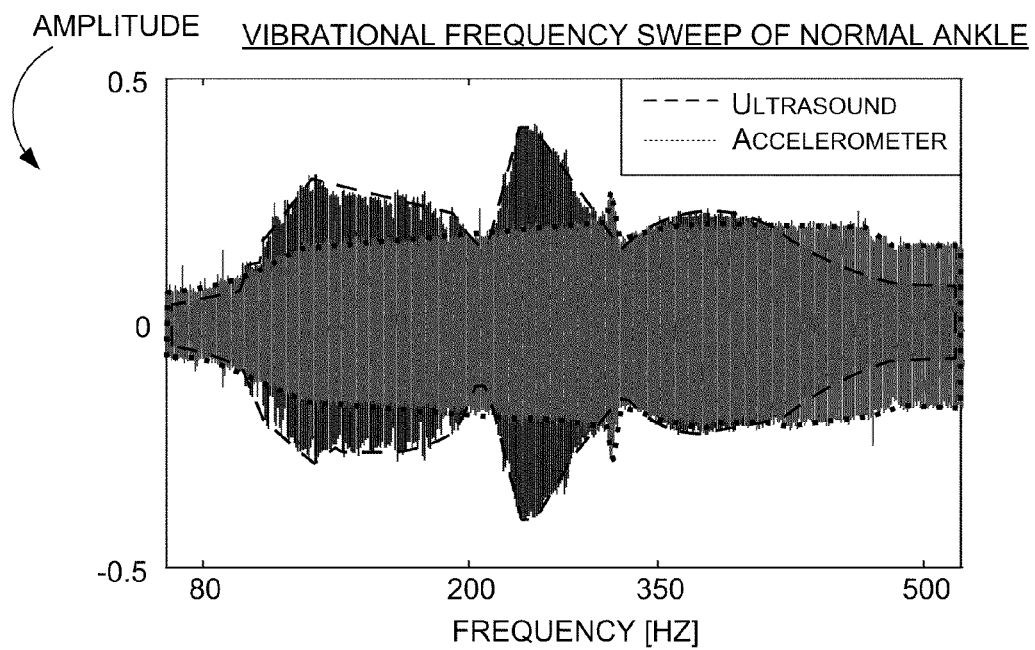
Figure 10:
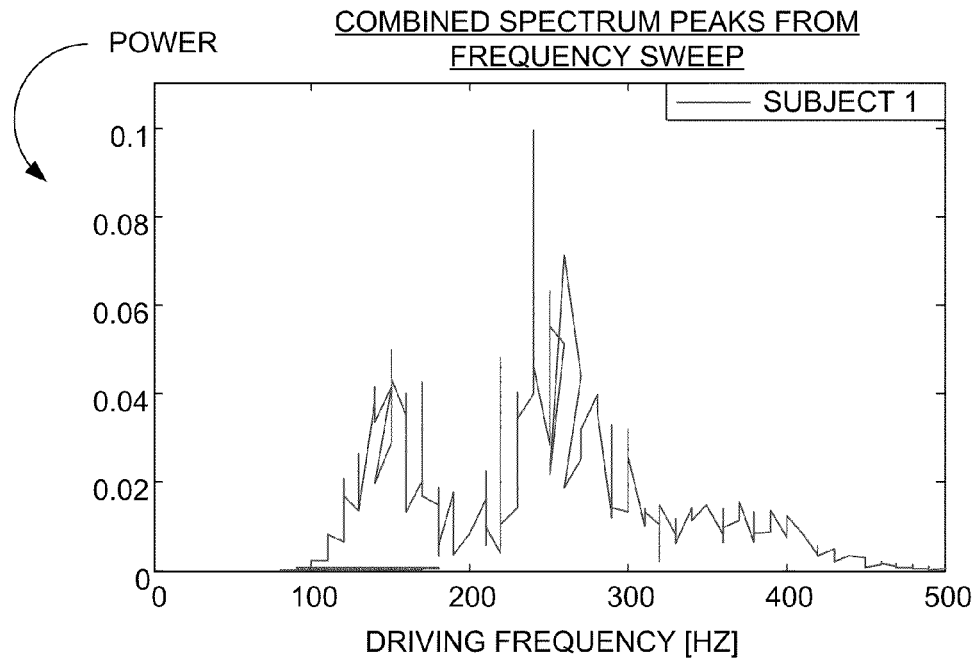
Figure 11:
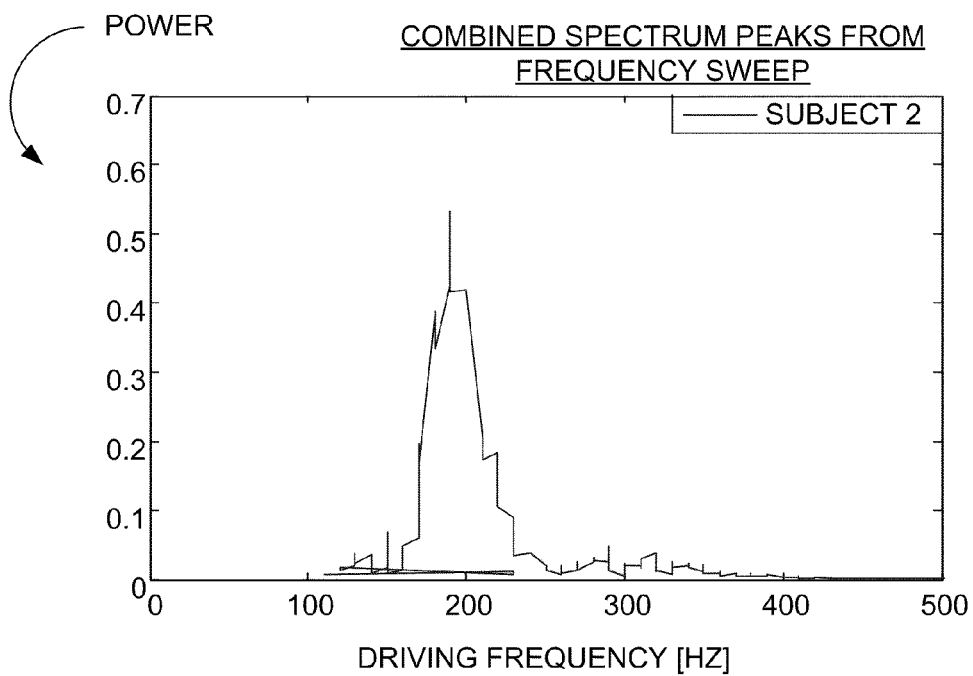
Figure 12:
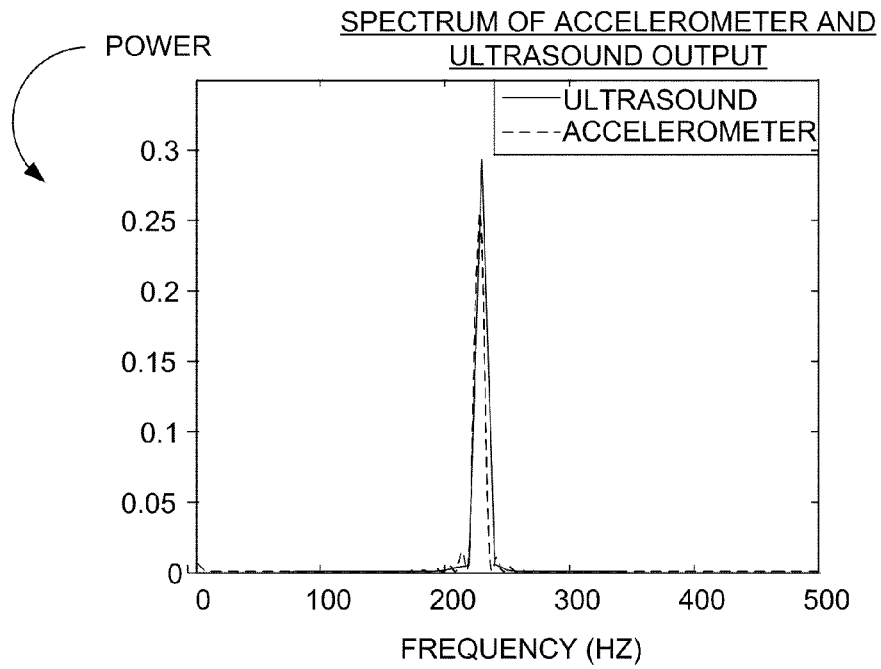
Figure 13:
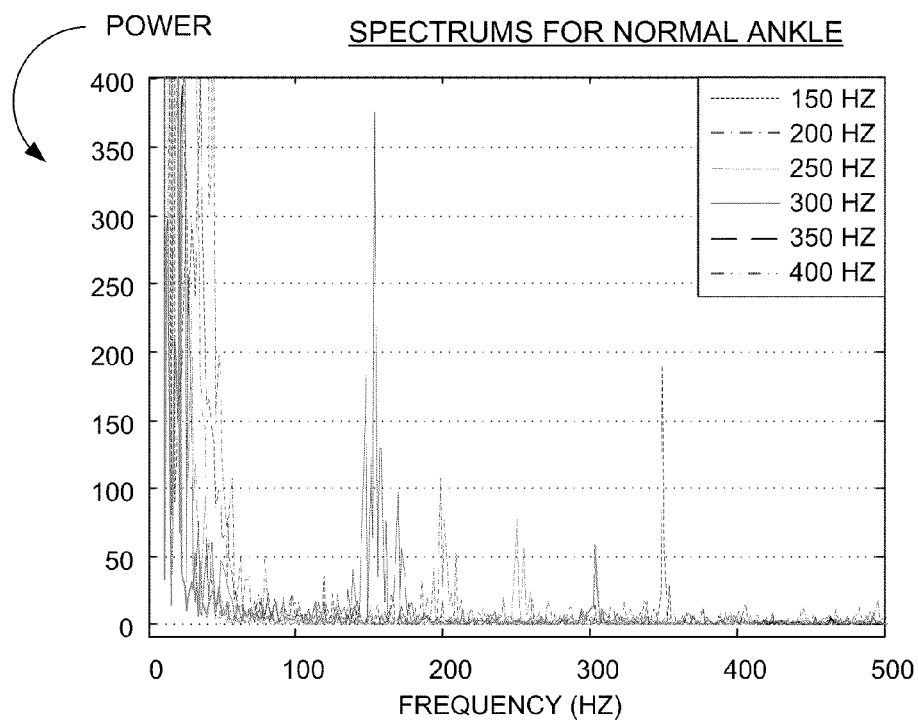
Figure 14A:
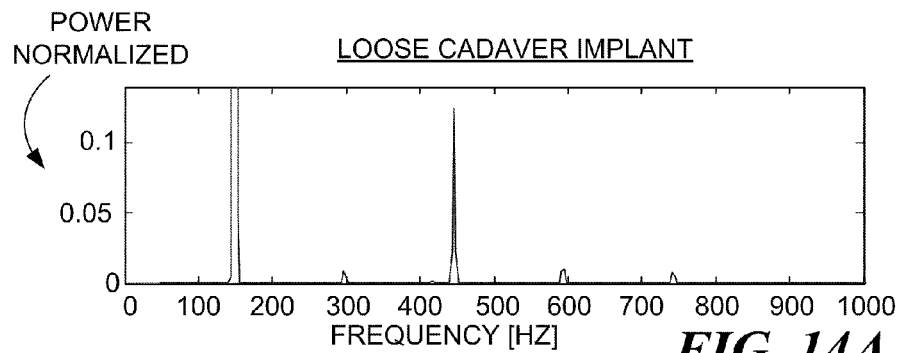
Figure 14B:
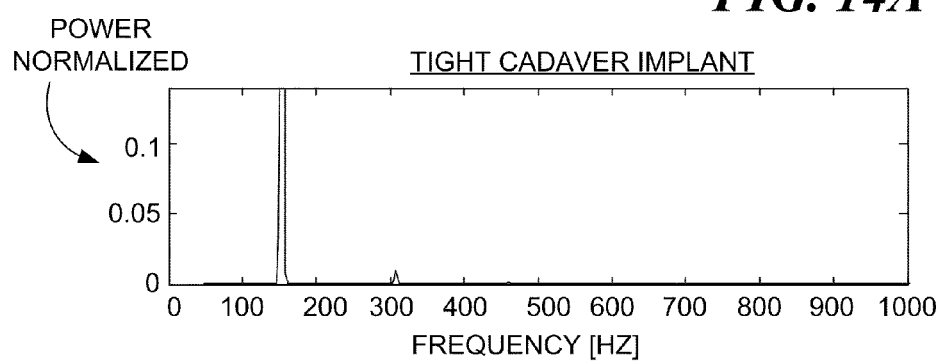
Figure 15A:
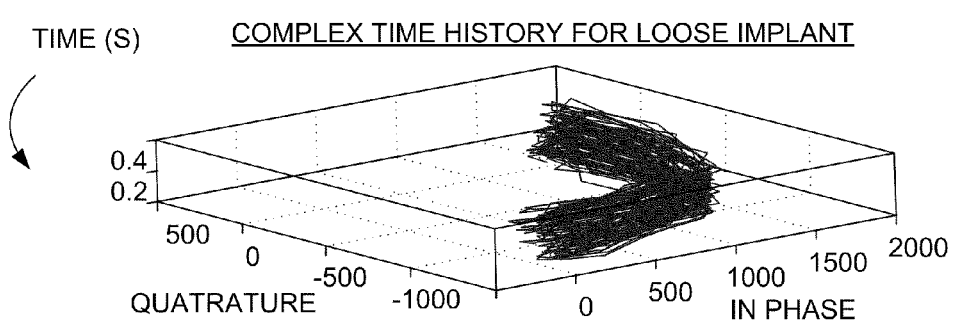
Figure 15B:
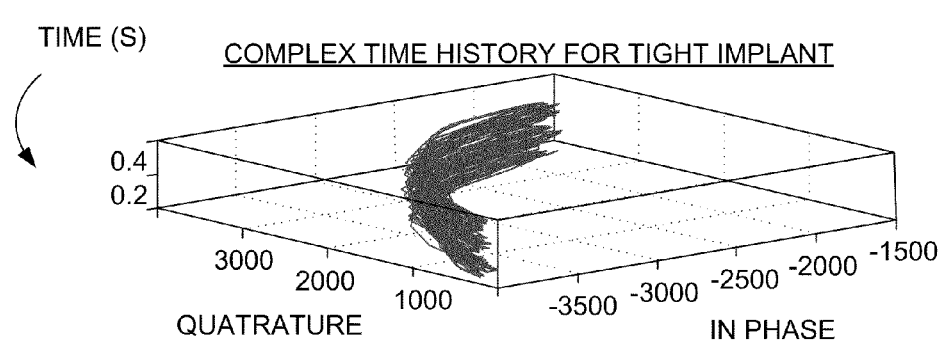
Figure 16:
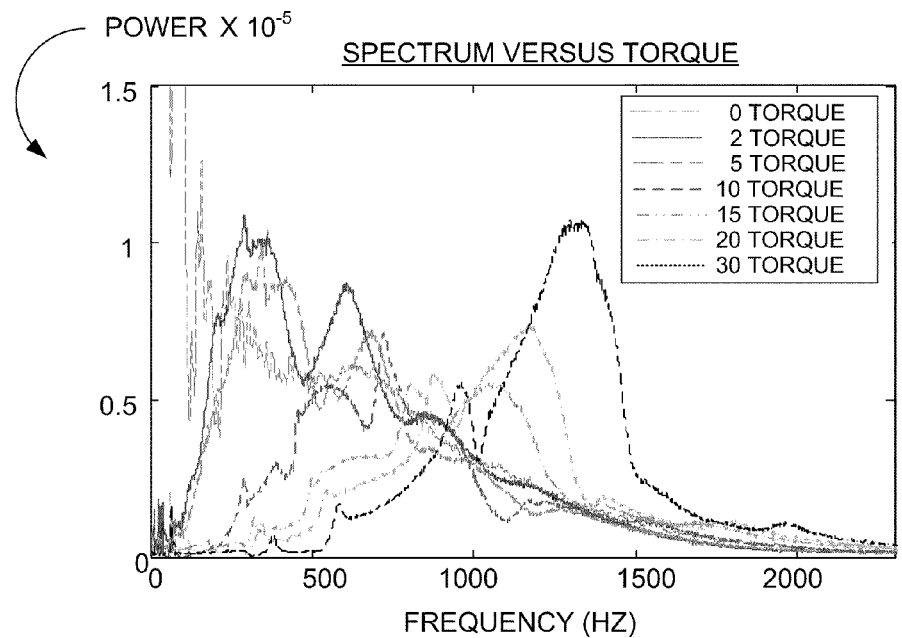
Figure 17A:
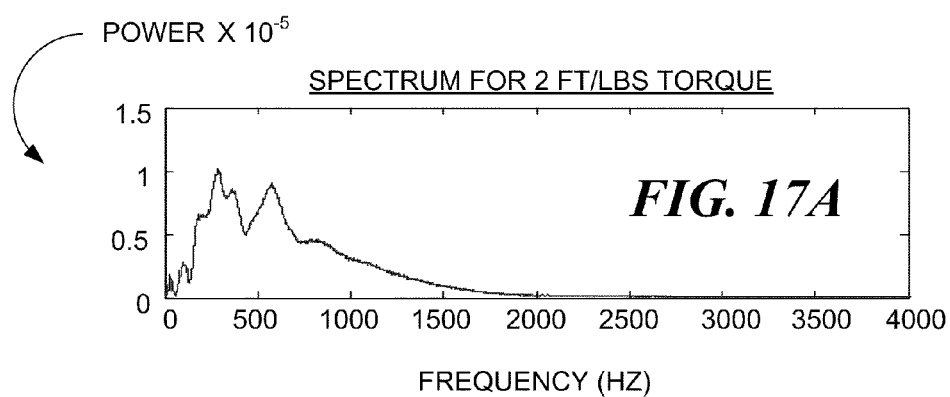
Figure 17B:
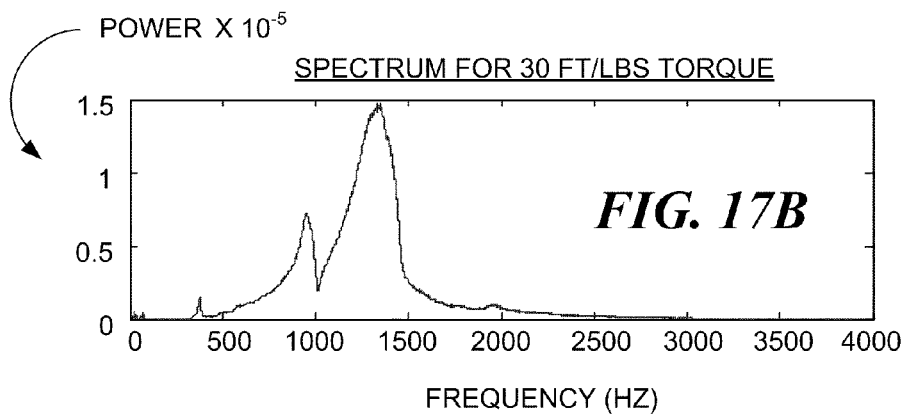

FIG. 5 schematically illustrates an ultrasound phantom constructed in order to simulate the mechanics of a loose or fixated medical implant system;

FIG. 6 graphically illustrates the time amplitude relationship for the phantom of FIG. 5 as measured using an accelerometer and ultrasound, wherein a solid line is a Doppler reading that is clipped due to too strong a signal;

FIG. 7A graphically illustrates the power and frequency spectrum of the phantom of FIG. 5 in a loose configuration, with the ultrasound probe being gated on the phantom and driven at about 194 Hz;

FIG. 7B graphically illustrates the power and frequency spectrum of the phantom of FIG. 5 in a loose configuration, with the ultrasound probe being gated and reading from off of the phantom;

FIG. 8 graphically illustrates the power and frequency spectrum of the phantom of FIG. 5 in a tight configuration, with the ultrasound probe being gated and reading from off of the phantom;

FIG. 9 graphically illustrates a time history of an 80-500 Hz frequency sweep of a first patient's ankle, indicating the amplitude and frequency spectrum as the ankle experiences induced vibration, where the resulting data are collected using both an accelerometer and ultrasound;

FIG. 10 graphically illustrates the power and frequency spectrum of a first patient's ankle experiencing an induced vibration, where the output data are collected using Doppler ultrasound;

FIG. 11 graphically illustrates the power and frequency spectrum of a second patient's ankle experiencing induced vibration, where the output data are collected using Doppler ultrasound;

FIG. 12 graphically illustrates the power and frequency spectrum of a first patient's ankle experiencing induced vibration, where the output data are collected using both an accelerometer and Doppler ultrasound, showing that Doppler ultrasound is able to read the frequency of the actuator's driving force;

FIG. 13 graphically illustrates the power and frequency spectrum of a second patient's ankle experiencing induced vibration at six different frequencies, where the output data are collected using ultrasound;

FIG. 14A graphically illustrates the normalized power and frequency spectrum of a loose cadaver implant undergoing induced vibration at 100 Hz, where the data are collected using ultrasound;

FIG. 14B graphically illustrates the normalized power and frequency spectrum of a tight cadaver implant undergoing induced vibration at 100 Hz, where the data are collected using ultrasound;

FIG. 15A graphically illustrates a complex time history of ultrasound data collected from a loose cadaver implant undergoing induced vibration at 100 Hz;

FIG. 15B graphically illustrates a complex time history of ultrasound data collected from a tight cadaver implant undergoing induced vibration at 100 Hz;

FIG. 16 graphically illustrates the power and frequency spectrum of a first exemplary model ankle implant undergoing induced vibration, where the data are collected using laser vibrometry at a plurality of different model torque settings;

FIG. 17A graphically illustrates the power and frequency spectrum of the first exemplary model ankle implant undergoing induced vibration, where the data are collected using laser vibrometry at a first model torque setting;

FIG. 17B graphically illustrates the power and frequency spectrum of the first exemplary model ankle implant undergoing induced vibration, where the data are collected using laser vibrometry at a second model torque setting.

Figure 18:
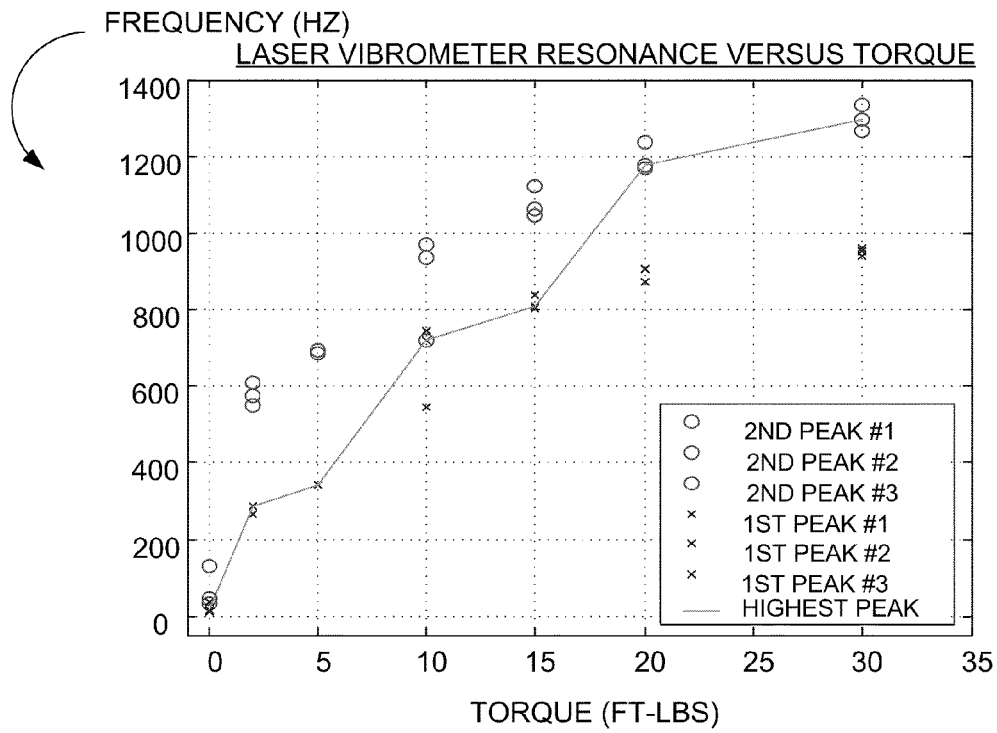
Figure 19:
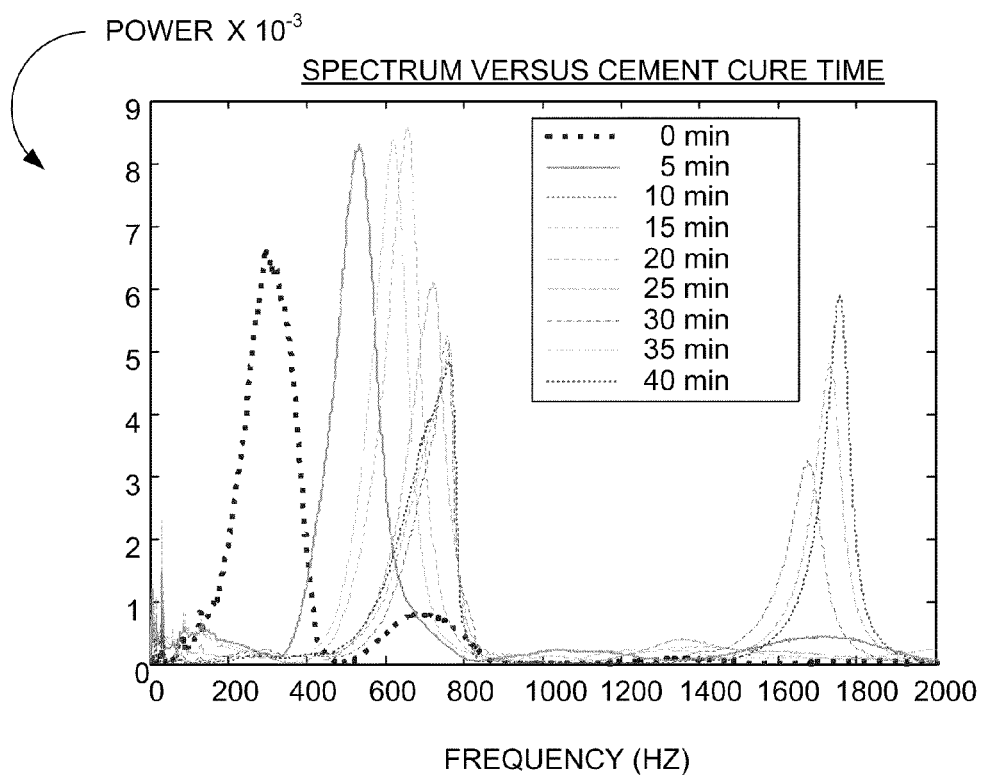
Figure 20:
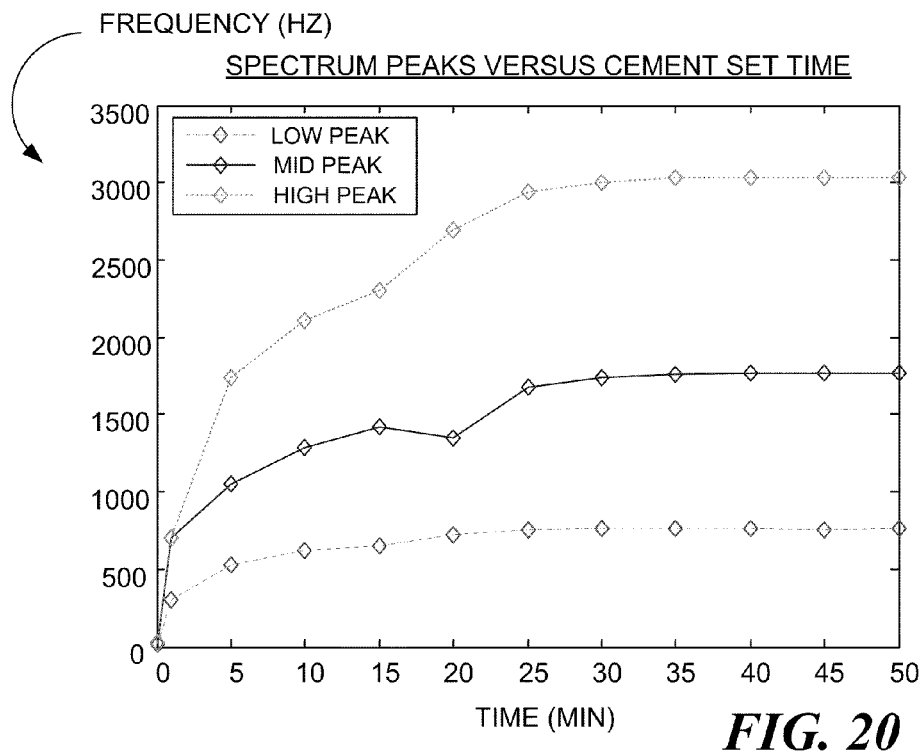
Figure 21:
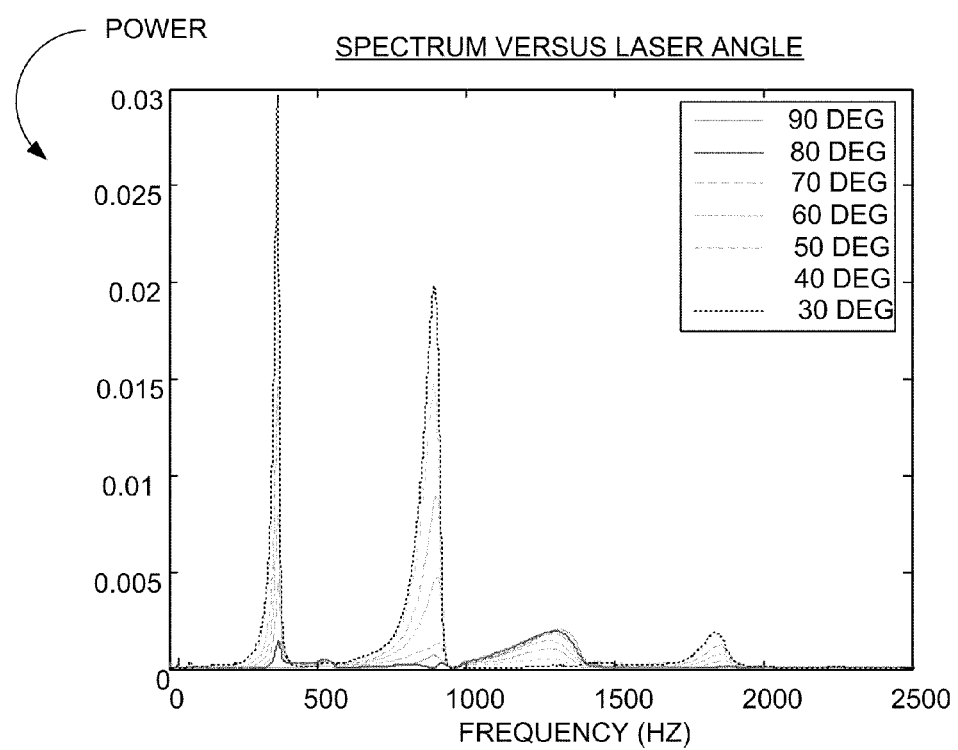
Figure 22:
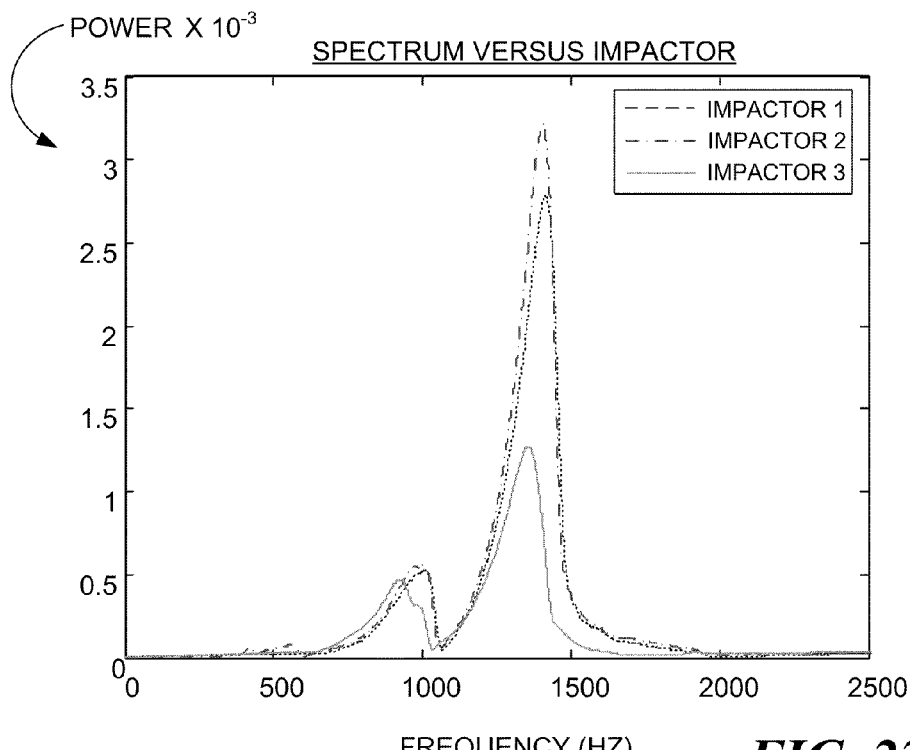
Figure 23:
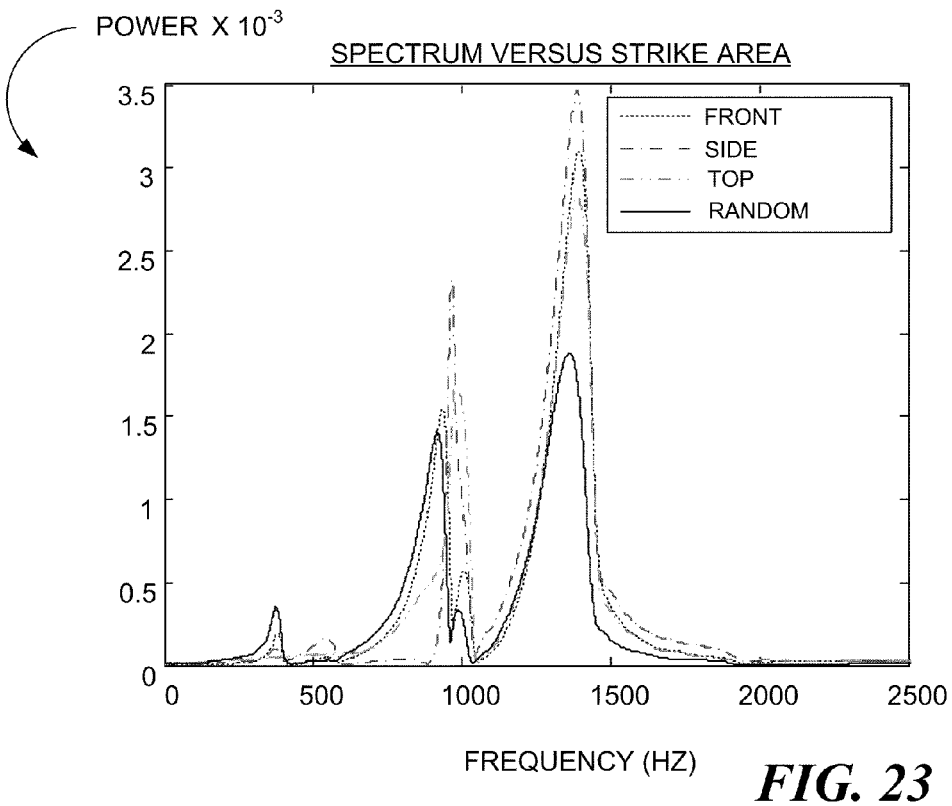
Figure 24:
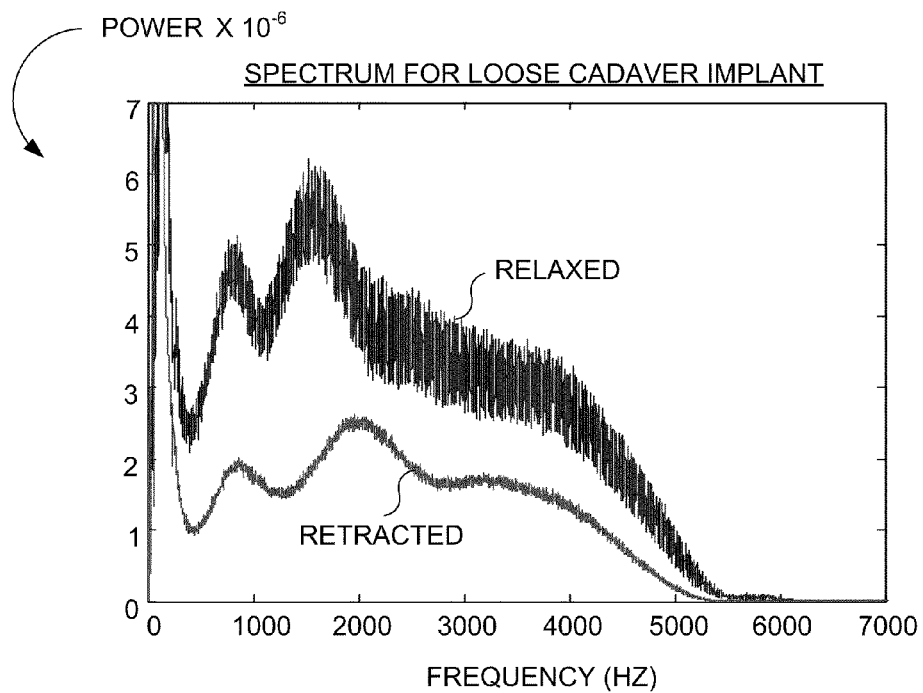
Figure 25:
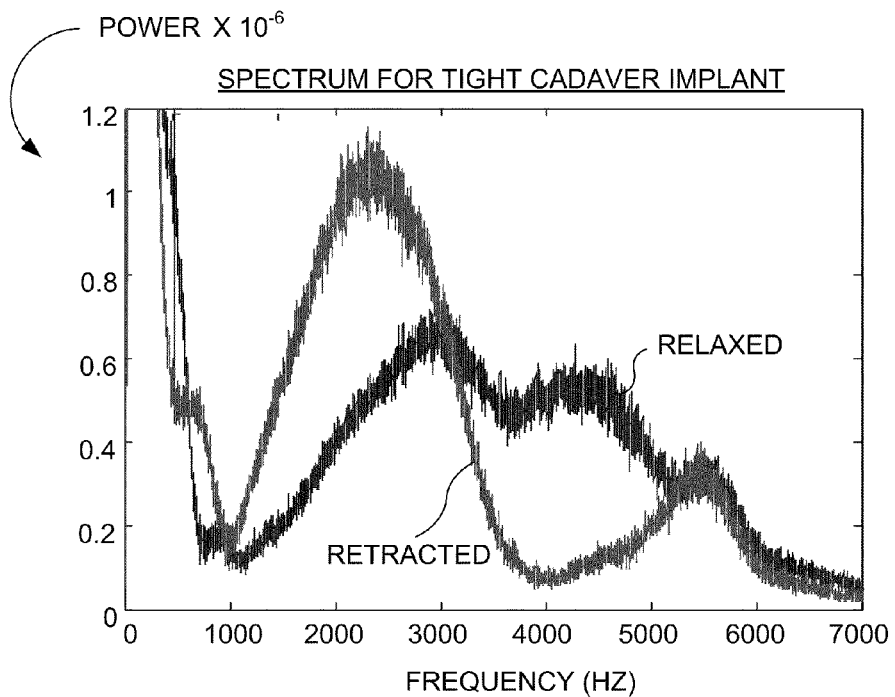
Figure 26:
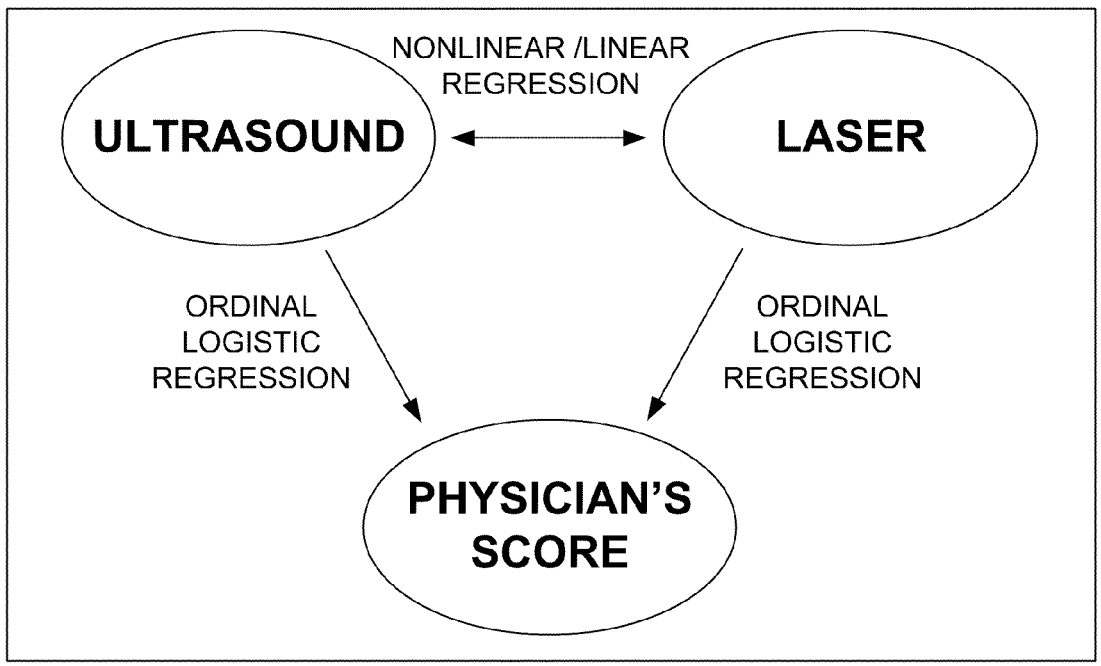
Figure 27:
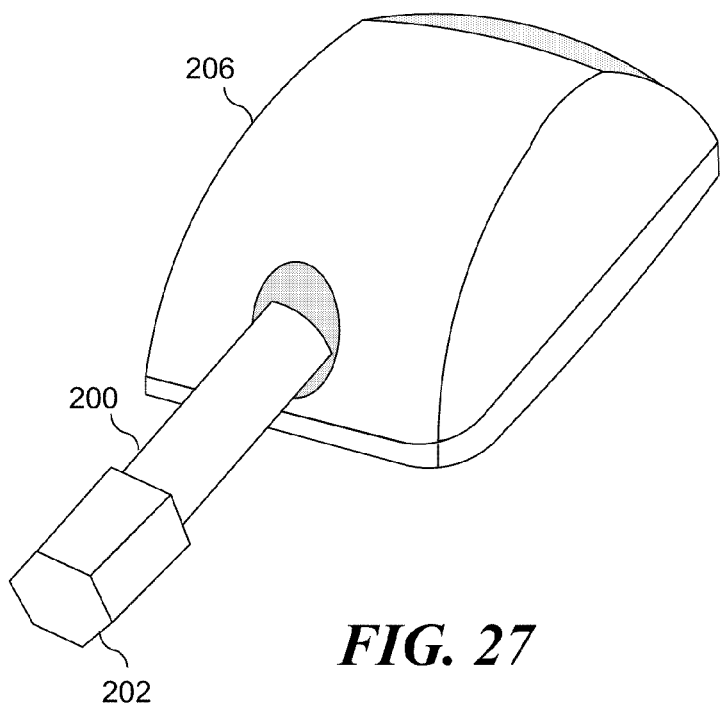
Figure 28:
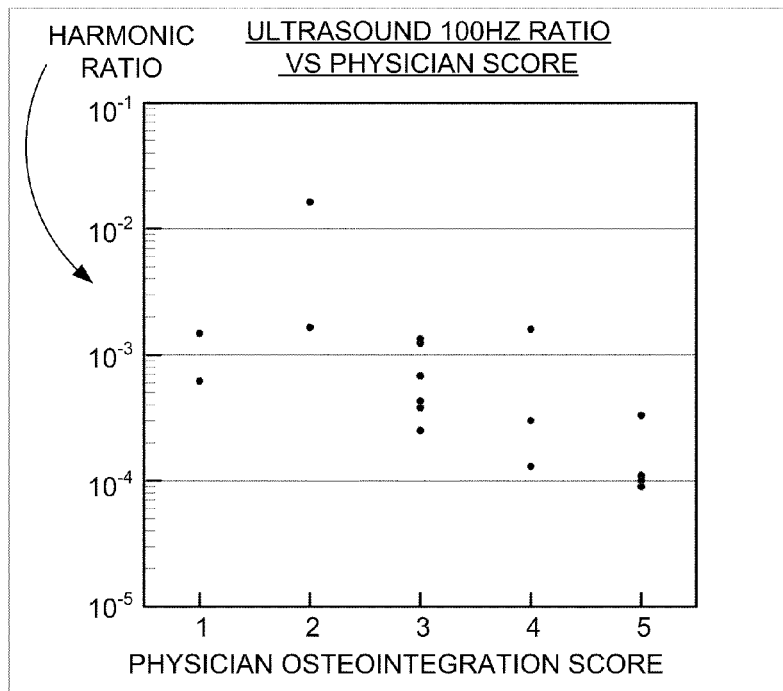
Figure 29:
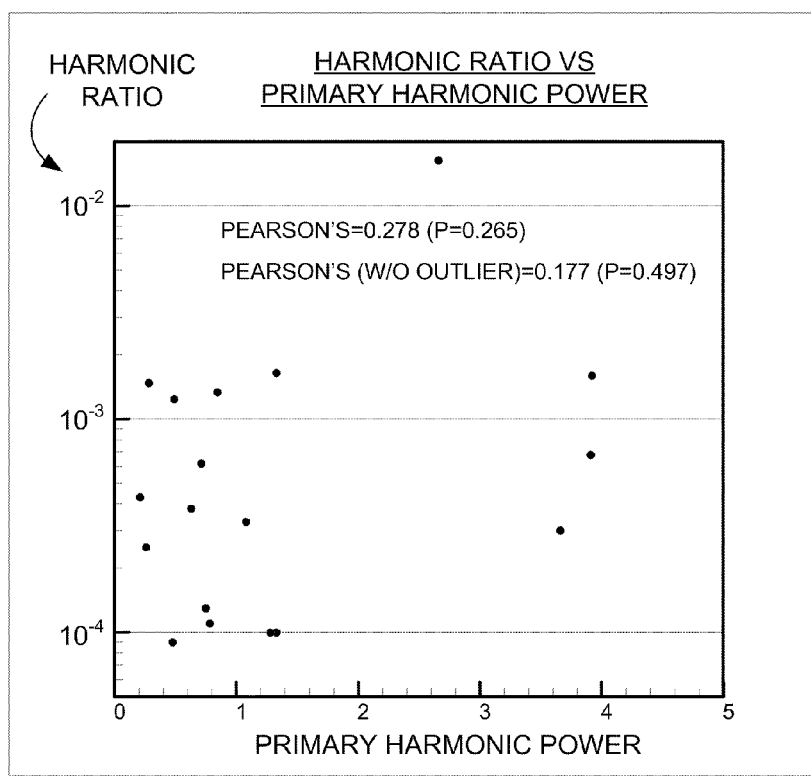
Figure 30:
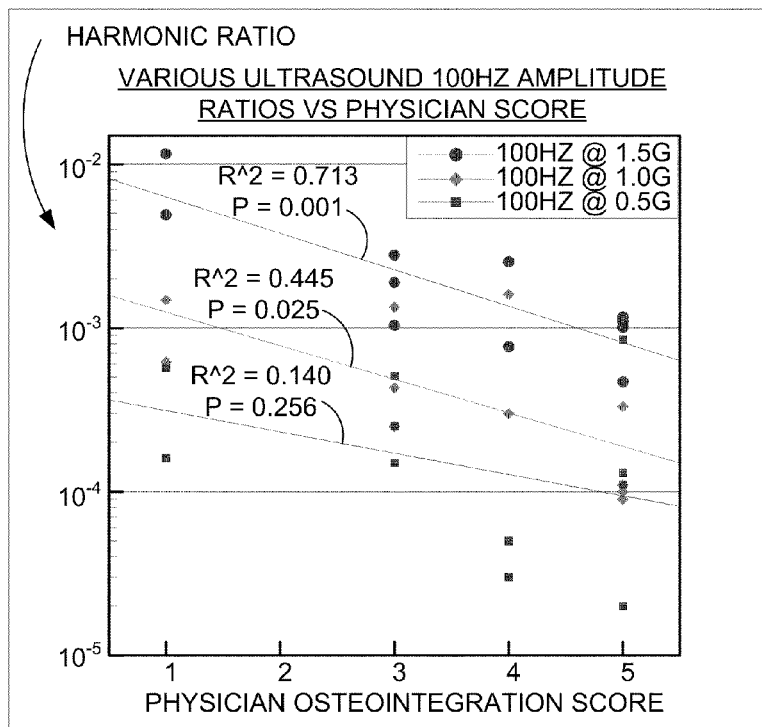
Figure 31:
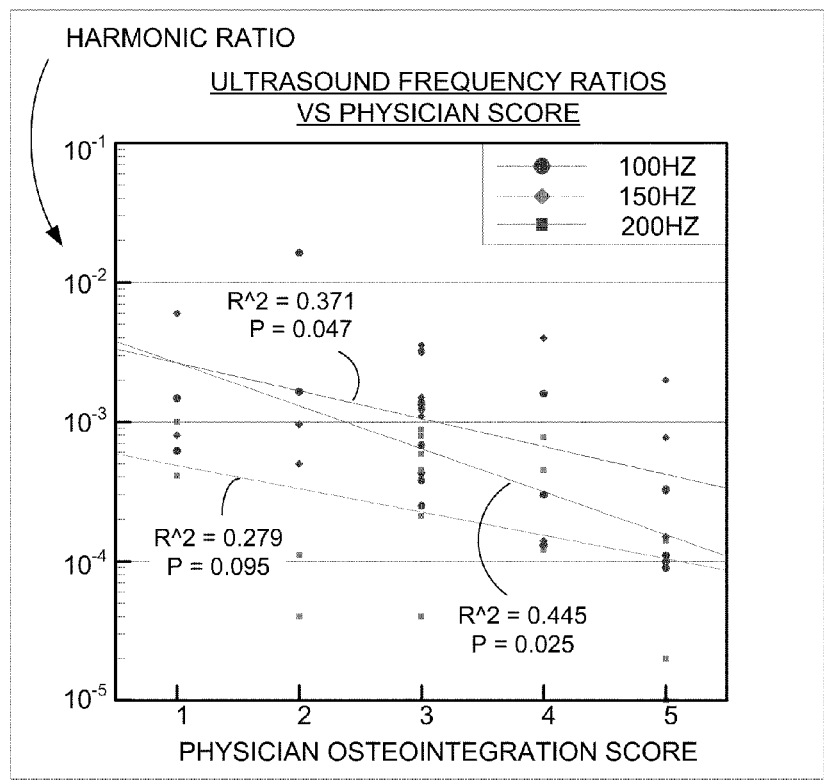
Figure 32:
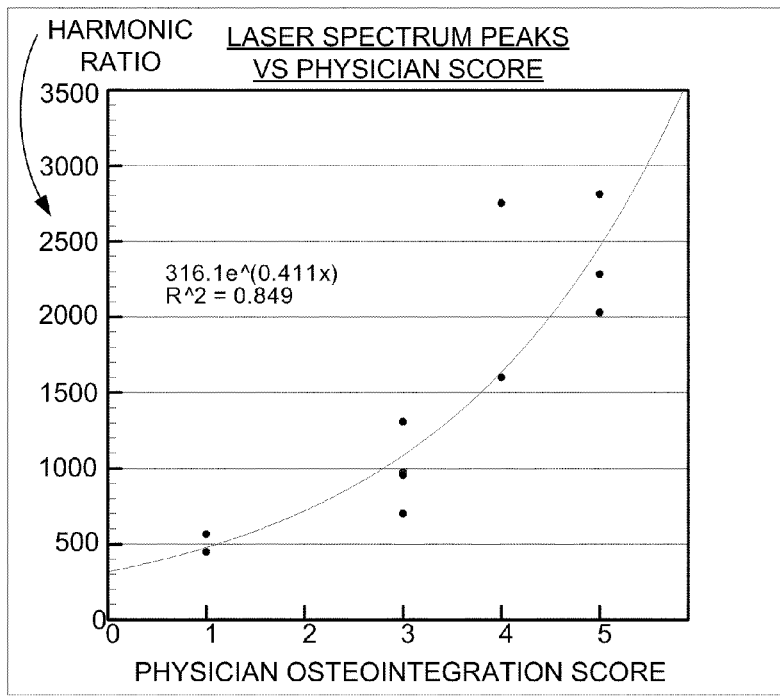
Figure 33:
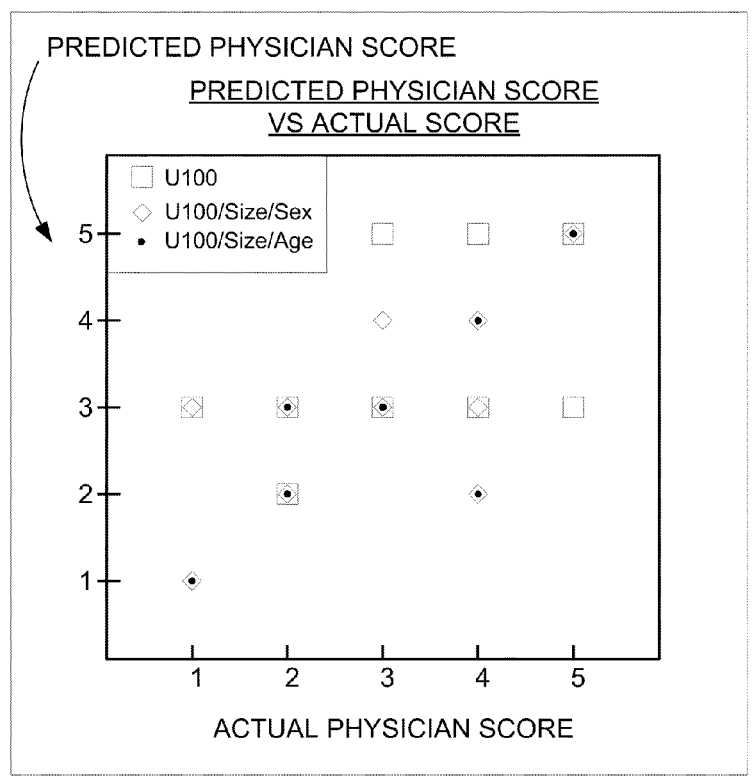
Figure 34:
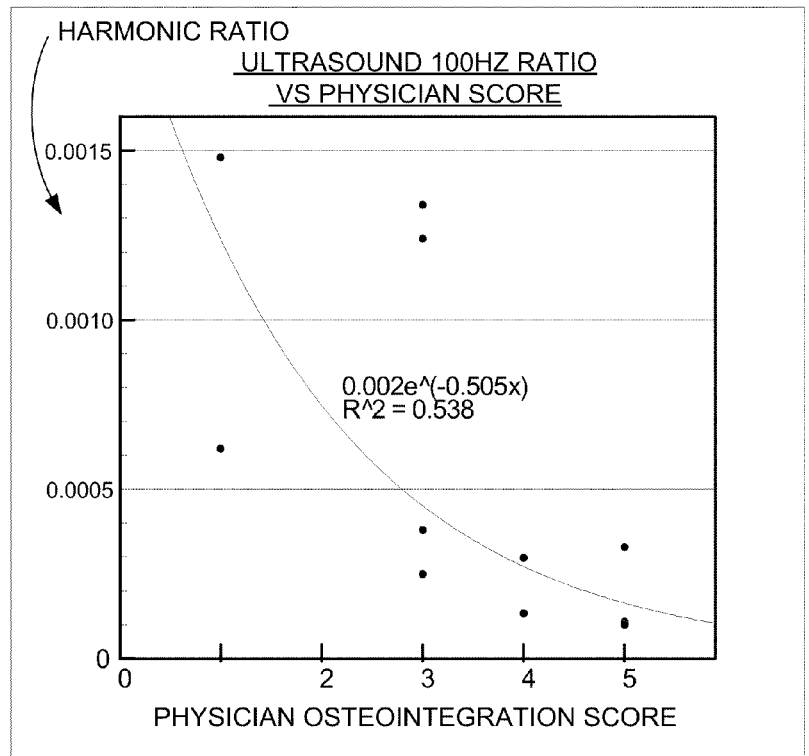
Figure 35:
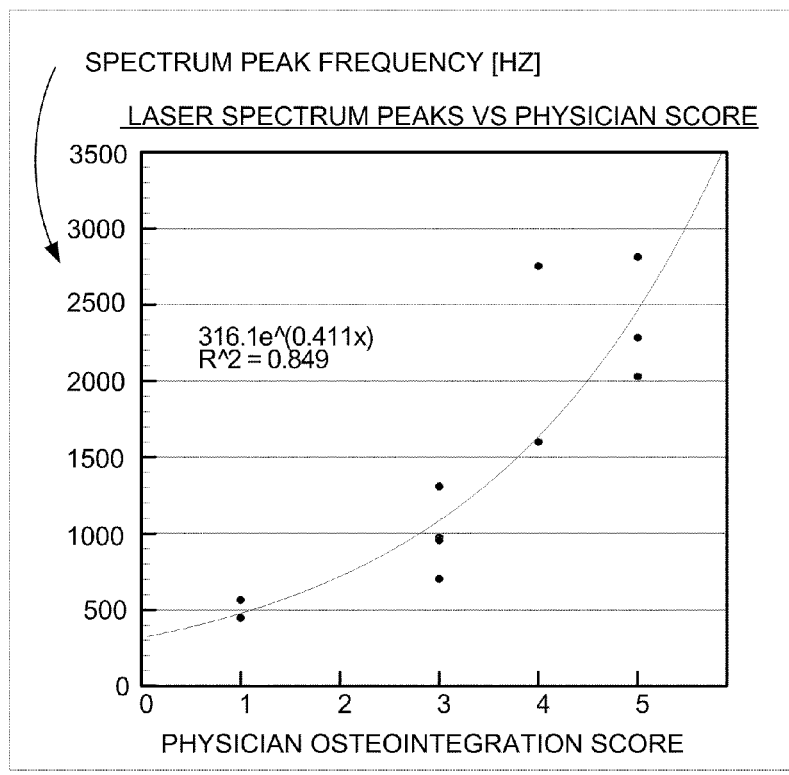
Figure 36:
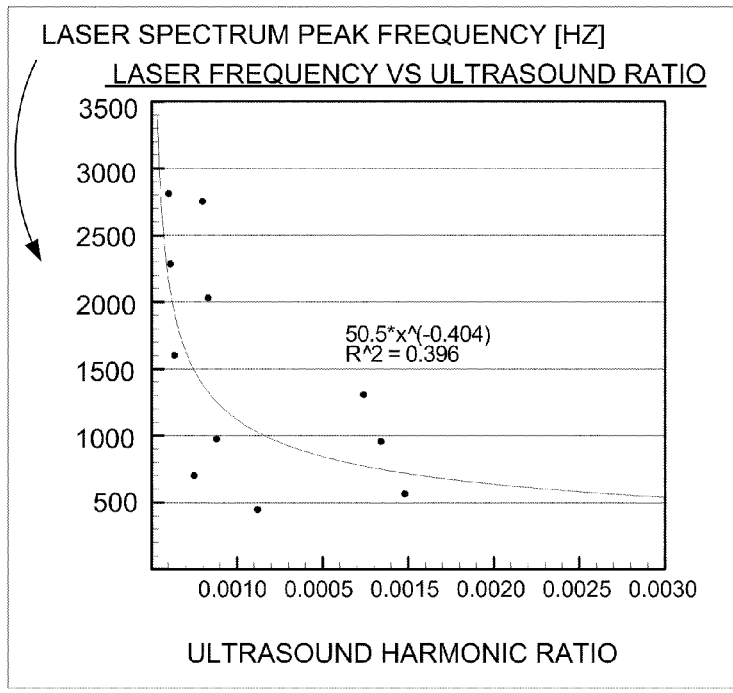
Figure 37:
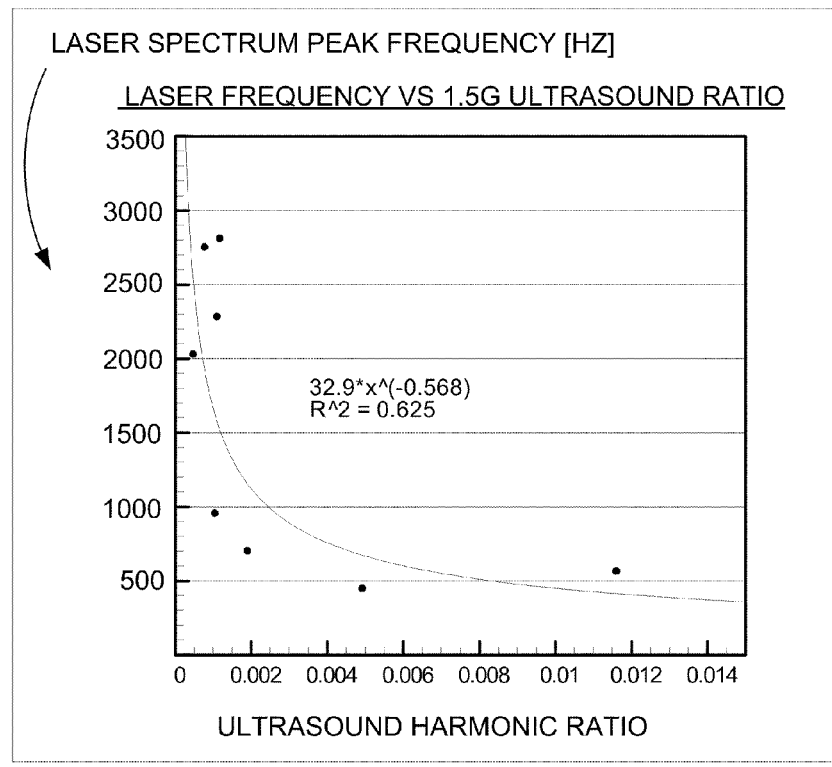
Figure 38:
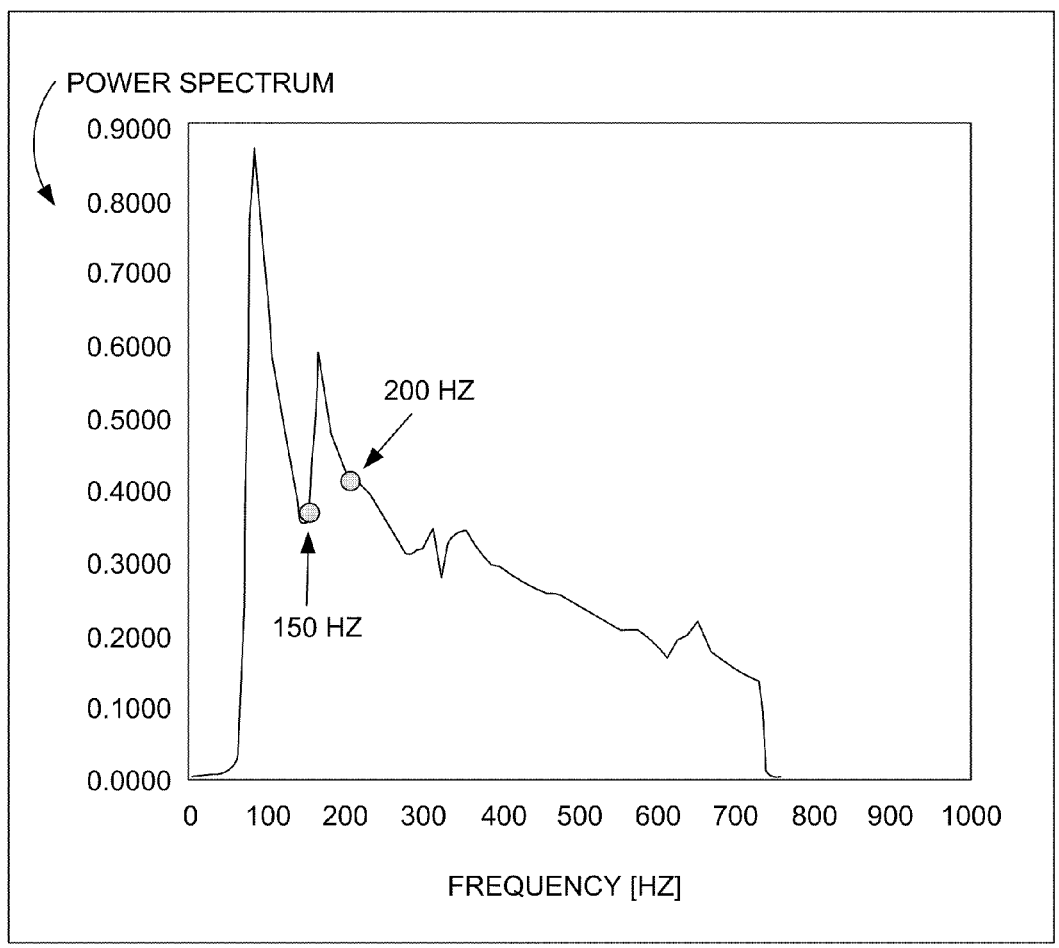

FIG. 18 graphically illustrates the torque and frequency spectrum of the first exemplary model ankle implant undergoing induced vibration, where the data are collected using laser vibrometry at a plurality of different model torque settings;

FIG. 19 graphically illustrates the power and frequency spectrum of a second exemplary model ankle implant undergoing induced vibration, where the data are collected using laser vibrometry at various cement cure times;

FIG. 20 graphically illustrates the time and frequency spectrum of the second exemplary model ankle implant undergoing induced vibration, where the data are collected using laser vibrometry at various cement cure times;

FIG. 21 graphically illustrates the power and frequency spectrum of the second exemplary model ankle implant undergoing induced vibration, where the data are collected using laser vibrometry at various laser incidence angles;

FIG. 22 graphically illustrates the power and frequency spectrum of the second exemplary model ankle implant undergoing induced vibration, where the data are collected using laser vibrometry, and three different impactors are used;

FIG. 23 graphically illustrates the power and frequency spectrum of the second exemplary model ankle implant undergoing induced vibration, where the data are collected using laser vibrometry, and different portions of the model are struck to induce the vibration;

FIG. 24 graphically illustrates the power and frequency spectrum of a loose ankle implant in a cadaver undergoing induced vibration, where the data are collected using laser vibrometry;

FIG. 25 graphically illustrates the power and frequency spectrum of a tight ankle implant in a cadaver undergoing induced vibration, where the data are collected using laser vibrometry;

FIG. 26 schematically illustrates a regression comparison between three different techniques used to evaluate the degree of osteointegration of an implant, including non-invasive ultrasound vibrometry, inter-operational laser vibrometry, and inter-operational physician scoring;

FIG. 27 schematically illustrates an exemplary cantilever added to a medical implant to facilitate laser vibrometry;

FIG. 28 graphically illustrates a scatter plot of harmonics ratio using a 100 MHz driving frequency, versus a physician's score corresponding to the degree of osteointegration as evaluated by the physician;

FIG. 29 graphically illustrates a scatter plot of harmonics ratio using a 100 MHz driving frequency, versus the intensity of the primary harmonic;

FIG. 30 graphically illustrates a scatter plot of various ultrasound amplitude ratios versus a physician's score corresponding to the degree of osteointegration as evaluated by the physician;

FIG. 31 graphically illustrates a scatter plot of various ultrasound frequency ratios versus a physician's score corresponding to the degree of osteointegration as evaluated by the physician;

FIG. 32 graphically illustrates a scatter plot of laser vibrometry spectrum peaks versus a physician's score corresponding to the degree of osteointegration as evaluated by the physician;

FIG. 33 graphically illustrates a scatter plot of predicted physician osteointegration scores versus actual physician osteointegration scores;

FIG. 34 graphically illustrates an exponential curve fit for down-sampled ultrasound vibrometry data versus actual physician osteointegration scores;

FIG. 35 graphically illustrates an exponential curve fit for laser vibrometry data versus actual physician osteointegration scores;

FIG. 36 graphically illustrates a power function curve fit for laser frequency data versus a first set of ultrasound harmonic ratio data, at 100 Hz vibration frequency;

FIG. 37 graphically illustrates a power function curve fit for laser frequency data versus a second set of 1.5 g ultrasound harmonic ratio data at 100 Hz, with a better goodness-of-fit than ultrasound data at 1.0 g; and FIG. 38 graphically illustrates a power and frequency relationship for the electromagnetic actuator used as a vibration source in the empirical studies.

Figure 39:
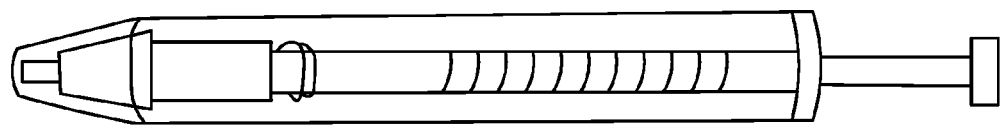

FIG. 39 illustrates an exemplary impactor pen.

Figure 40:
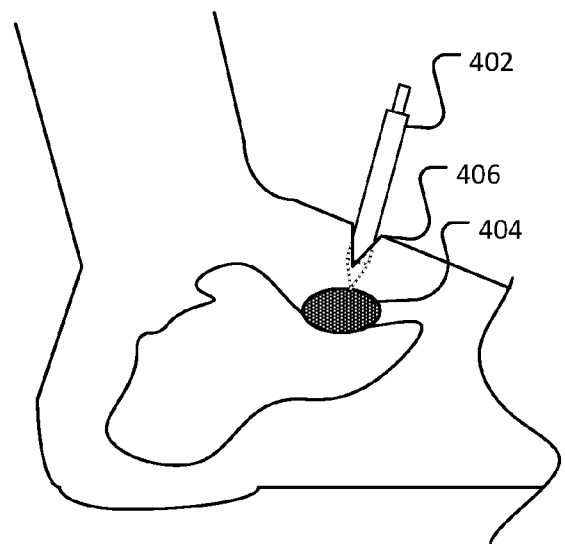

FIG. 40 schematically illustrates an exemplary impact pen in contact with an implant via a surgical wound.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

Overview of the Novel Concepts

Figure 1:
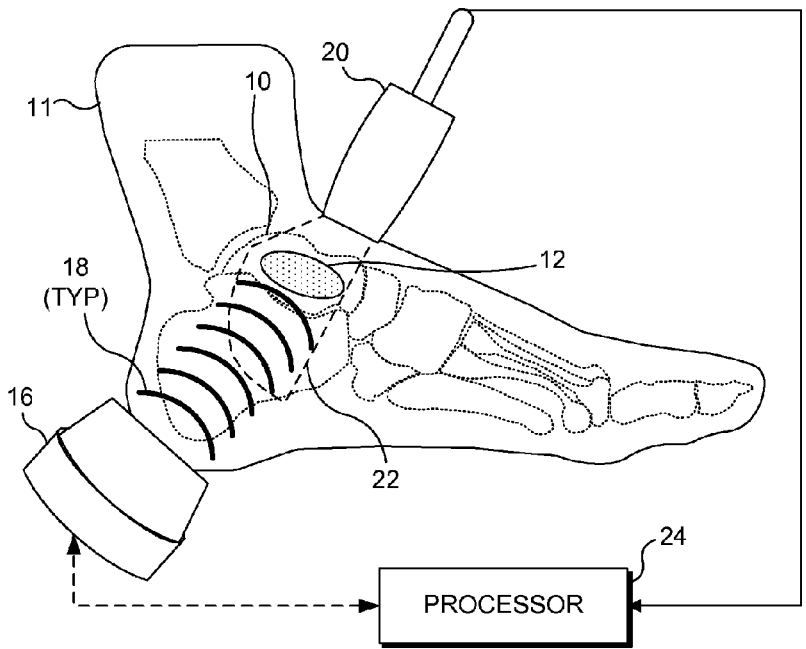

FIG. 1 schematically illustrates an ultrasound probe being used to non-invasively collect data that can be used to evaluate the degree of osteointegration of a medical implant. As illustrated therein, a medical implant 12 (such as an artificial ankle joint) has been implanted into a patient's foot 11, proximate to talus bone 10. It should be understood that implant 12 is represented schematically, and no attempt has been made to accurately portray the size, shape, or location of the implant. For example, actual artificial ankle joints can be provided to replace some or all of the talus bone. However, for the purposes of broadly disclosing the novel concepts that have been developed, this schematic representation should be acceptable. It should also be recognized that while the concepts disclosed herein are particularly well suited to evaluating the degree of osteointegration of artificial ankle joints, these concepts can also be employed to evaluate the degree of osteointegration of other medical implants.

A vibration source 16 (such as an electromagnetic actuator) is disposed proximate to the heel to direct vibrations 18 into foot 11. An ultrasound probe 20 is disposed externally, proximate talus bone 10 and implant 12, such that the implant is (at least partially) within a window 22 of the ultrasound probe. The ultrasound probe collects data indicating how the implant changes the vibrations induced by vibration source 16. A processor 24 is logically coupled to ultrasound probe 20 (or to an ultrasound machine, not shown, to which the ultrasound probe is directly coupled), to analyze the ultrasound data being collected, to evaluate the degree of osteointegration of the implant.

Figure 2:
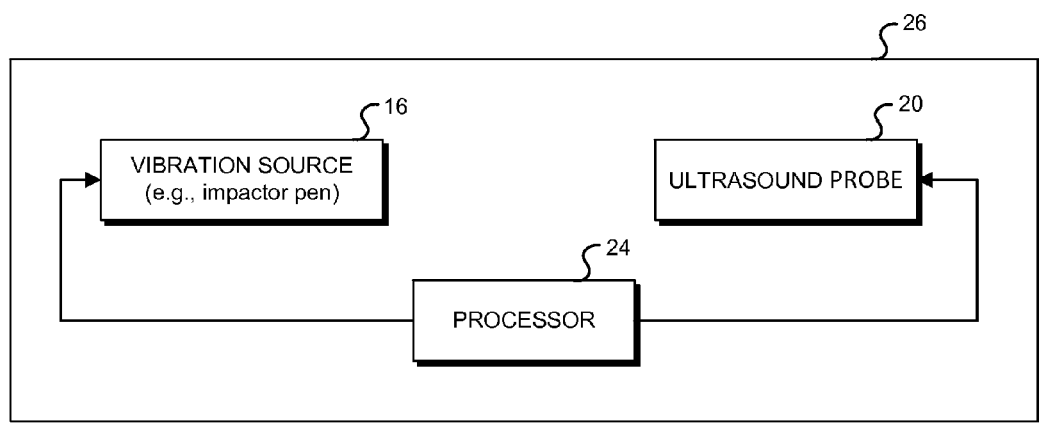
FIG. 2 is a functional block diagram of an exemplary system for using ultrasound to non-invasively collect data that can be used to evaluate a degree of osteointegration of a medical implant.

FIG. 2 is a functional block diagram of an exemplary system 26 for using ultrasound to non-invasively collect data that can be used to evaluate the degree of osteointegration of a medical implant. System 26 includes vibration source 16, ultrasound probe 20, and processor 24. Note that ultrasound probes are typically designed to be used with a specific ultrasound machine that itself includes a processor. While processor 24 could be the same processor as that included within the ultrasound machine being used with ultrasound probe 20, it should be recognized that processor 24 can also be a separate processor. Also, processor 24 can be one used in a personal computer. It should also be recognized that processor 24 can be implemented using hardware alone (e.g., a dedicated processing circuit that does not require machine instructions to be loaded into a memory), such as an application specific integrated circuit.

Figure 3:
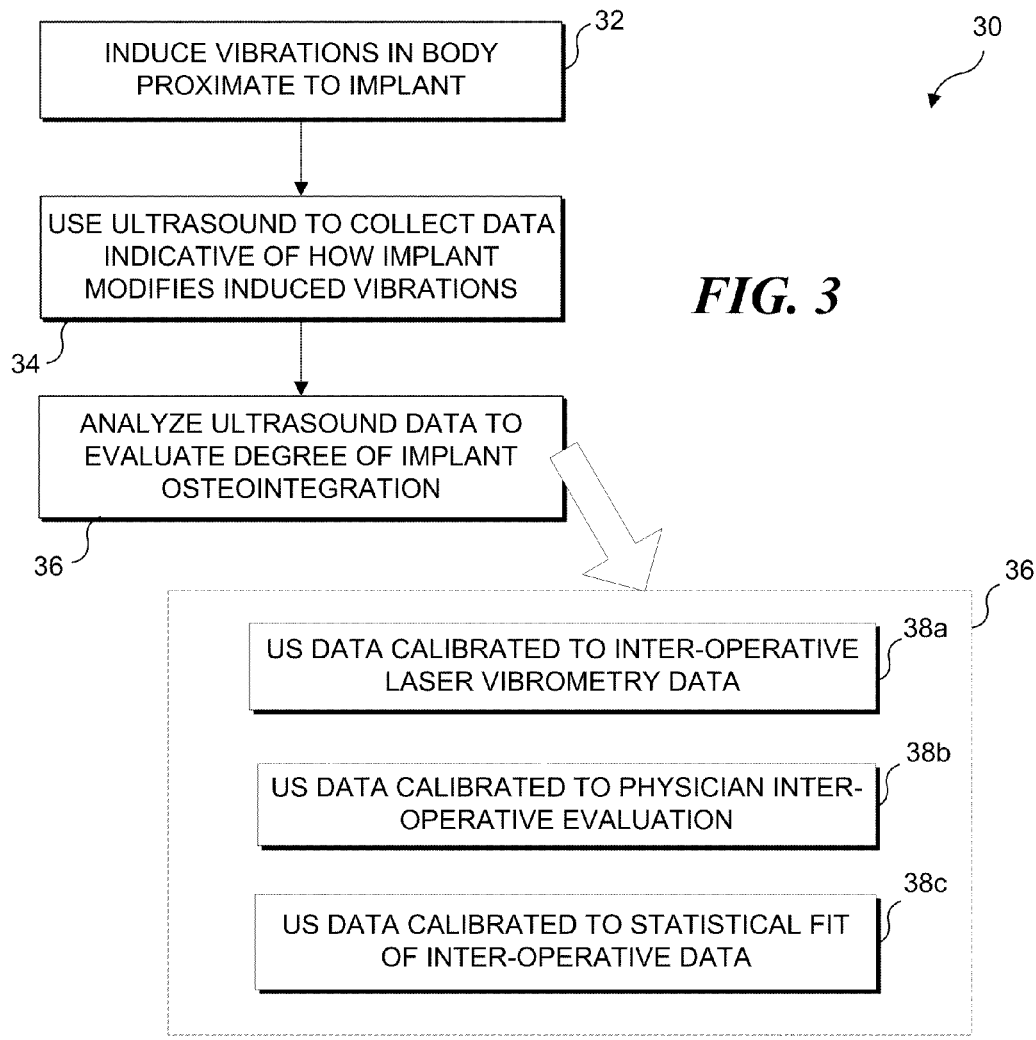
FIG. 3 is a flow chart illustrating exemplary steps for using ultrasound to evaluate a degree of osteointegration of a medical implant.

FIG. 3 is a flow chart 30 illustrating exemplary steps for using ultrasound to evaluate a degree of osteointegration of a medical implant. In a block 32, vibrations are induced in the patient's body proximate to the implant to be evaluated. In a block 34, ultrasound propagating through this portion of the patient's body is used to collect data indicating how the implant modifies the induced vibrations (or more specifically, how the bond between the implant and the patient's bone structure modifies the induced vibrations). In a block 36, the ultrasound data are analyzed to evaluate the degree of osteointegration of the implant. Such an evaluation will ensure that patients are instructed to avoid applying normal stresses to the implant until sufficient osteointegration has occurred. Additionally, this evaluation would be useful in helping a clinician assess whether post-operative pain may be due to a loose (i.e., poorly integrated) implant.

Note that FIG. 3 includes an expanded view of block 36, providing further details indicating how the analysis of the ultrasound data is implemented. As discussed in detail below, a calibration factor or reference needs to be provided as a baseline to which the ultrasound data can be compared. In a block 38a, the ultrasound data are calibrated to laser vibrometry data obtained during an inter-operative procedure. In a block 38b, the ultrasound data are calibrated in regard to a physician-provided osteointegration evaluation carried out during an intra-operative procedure. In a block 38c, the ultrasound data are calibrated to a statistical fit of additional data obtained during an intra-operative procedure. Other calibration techniques (in addition to laser vibrometry and physician assessment) could be used, thus, calibration based on laser vibrometry and physician assessment are intended to be exemplary, and not limiting.

For example, histological analysis of a retrieved implant might also be used to calibrate the ultrasound vibrometry data. Histological analysis of the retrieved implant (i.e., "an explant") could be performed to establish actual amounts of bony in-growth (osteointegration) into the porous implant surface of the implant. Another potential calibration technique would be to employ in vivo mechanical testing of an implant (for example, prior to removal of a failed implant) to calibrate previously collected ultrasound vibrometry data for that specific implant to the degree of osteointegration of that implant. This would involve applying some known (measureable) force vector (magnitude and direction) to the implant while recording the resulting displacement vector (magnitude and direction). This is similar to the laser vibrometry technique, but instead of vibrating the implant with a impactor, such a technique would involve pressing against the implant in select directions and recording the amount of implant movement the applied force caused. Another variation of the intra-operative laser vibrometry technique would be an intra-operative acoustic technique, in which the same impact is applied to the implant, and the acoustic signature emitted by the implant is recorded (as opposed to recording the reflected laser energy). Still another calibration technique is based on forensic examination of cadavers including such implants to determine the degree of implant osteointegration (after first making Doppler ultrasound vibrometry measurements of such implants).

Figure 4:
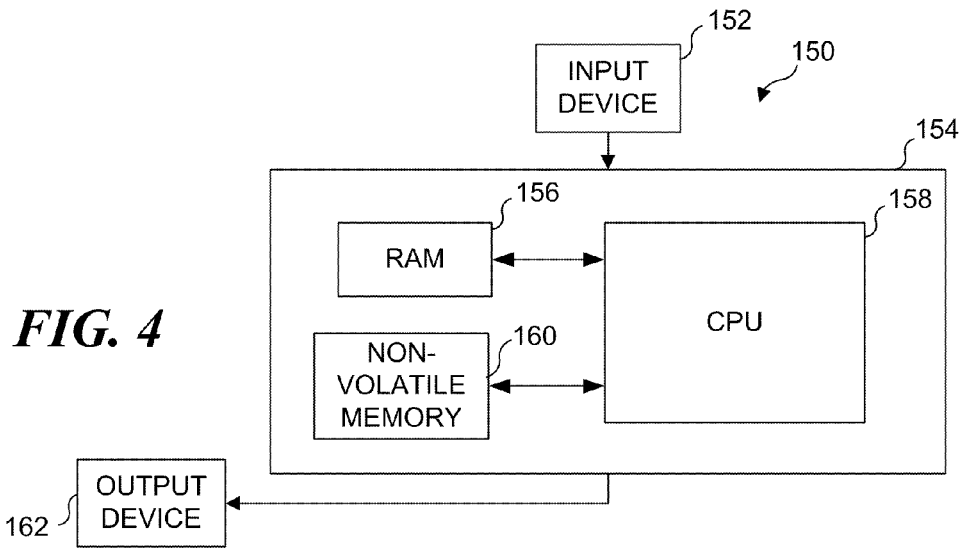
FIG. 4 is a functional block diagram of an exemplary computing system used to analyze ultrasound data to evaluate a degree of osteointegration of a medical implant.

FIG. 4 and the following related discussion are intended to provide a brief, general description of a suitable computing environment for analyzing ultrasound data to evaluate a degree of osteointegration of a medical implant, where processor 24 is implemented as a computing device (as opposed to a circuit). Those skilled in the art will appreciate that the processor may be implemented by many different types of computing devices, including a laptop and other portable computers, multiprocessor systems, networked computers, mainframe computers, hand-held computers, personal data assistants (PDAs), and on other types of computing devices that include a processor and a memory for storing machine instructions which when implemented by the processor result in the execution of a plurality of functions. In at least one embodiment, those functions are generally consistent with the functions implemented by processor 24 of FIGS. 1 and 2.

An exemplary computing system 150 suitable for implementing the steps of the method includes a processing unit 154 that is functionally coupled to an input device 152, and an output device 162, e.g., a display. Processing unit 154 includes a central processing unit (CPU 158, e.g., corresponding to processor 24) that executes machine instructions comprising a signal processing program for implementing the functions of processing ultrasound signals received by an ultrasound probe to evaluate a degree of osteointegration of a medical implant. CPUs suitable for this purpose are available, for example, from Intel Corporation, AMD Corporation, Motorola Corporation, and other sources.

Also included in processing unit 154 are a random access memory (RAM) 156 and a non-volatile memory 160, which typically includes read-only memory (ROM) and some form of memory storage, such as a hard drive, optical drive, etc. These memory devices are bi-directionally coupled to CPU 158. Such memory storage devices are well known in the art. Machine instructions and data are temporarily loaded into RAM 156 from non-volatile memory 160. Also stored in the non-volatile memory are the operating system software and ancillary software. While not separately shown, it will be understood that a generally conventional power supply will be included to provide the electrical power needed to energize computing system 150.

Input device 152 can be any device or mechanism that facilitates user input, including, but not limited to, a mouse or other pointing device, a keyboard, a microphone, a modem, a touch pad, or other input device. In general, the input device will be used to initially configure computing system 150 so that it is usable to achieve the desired signal processing (i.e., to evaluate a degree of osteointegration of a medical implant based on ultrasound imaging signals). While not specifically shown in FIG. 4, it should be understood that computing system 150 is logically coupled to ultrasound probe 20 (see FIGS. 1 and 2), for example, through a probe interface (not shown). Configuration of computing system 150 to achieve the desired signal processing includes the steps of storing appropriate signal processing software in non-volatile memory 160, and executing the signal processing application (i.e., loading the signal processing software into RAM 156 for execution by CPU 158) so that the signal processing application is ready for use. Output device 162 generally includes any device that produces output information, but will most typically comprise a monitor or computer display designed for human perception of output.

Vibrometry Fundamentals

The second law of motion, translated as "The rate of change of momentum of a body is proportional to the resultant force acting on the body and is in the same direction." can be expressed as the following equation:

$$\vec{F} = \frac{d\vec{p}}{dt} \quad (1)$$
$$= \frac{d(m\vec{v})}{dt}$$
$$= m\vec{a}$$

where F is the force produced, p is momentum, m is mass, v is velocity, and a is acceleration.

The right hand side of Eq. (1) simplifies when mass is held constant, thus relating the motion (acceleration) of an object to the force applied. This equation is the building block for constructing the equation of motion for a given system. The equation of motion is constructed using geometrical constraints, Newton's force-dynamic requirements, and the constitutive equations that relate forces to their origins in the physical characteristics of the system. The way a system responds to an input of energy depends upon the physical make-up of the system. These physical characteristics consist of such properties as mass, stiffness, geometry and dampening characteristics. Adding up the individual forces present in the system provides the following equation:

$$\sum_{i=1}^{q} f_i = \frac{dp_j}{dt} \quad (2)$$
$$= m_j a_j$$

where q is the total number of individual forces for each momentum j, which simplifies to individual forces per mass in the system, for constant mass.

Using the simple example of a one mass system incorporating stiffness and dampening and denoting all kinematics as derivatives of position, one arrives at the differential equation of motion:

$$f(t) - b\dot{x}(t) - kx(t) = m\ddot{x}(t) \quad (3)$$

involving a forcing function f(t) and two internal forces, which are functions of position and velocity. The constants b and k refer to the damping coefficient and stiffness of the system respectively. Eq. (3) is usually presented in the following standard form:

$$m\ddot{x}(t) + b\dot{x}(t) + kx(t) = f(t) \quad (4)$$

The forcing function f(t) of Eq. (4) is usually presented as a sinusoid with the equation:

$$f(t) = F_o \cos(2\pi ft) = RE\{F_o e^{i(2\pi ft)}\} \quad (5)$$

where $F_o$ is amplitude, and f is frequency.

The exponential form of the driving sinusoid in Eq. (5) is derived from the real part of the Euler identity. This approach is advantageous due to the fact that the exponential function is an eigenfunction of the differential operator d/dt, which greatly simplifies the mathematics involved in the derivation of the equation of motion. In a linear time invariant system, the output of the system will be proportional to the input and have the same frequency at steady state. Thus:

$$x(t) = Xe^{i(2\pi ft)}$$

$$\dot{x}(t) = i2\pi f Xe^{i(2\pi ft)}$$

$$\ddot{x}(t) = -(2\pi f)^2 Xe^{i(2\pi ft)} \quad (6a\text{-}6c)$$

Eqs. (6a-6c), which respectively define the position, velocity, and acceleration, incorporate the same variables as the forcing function, where X is the amplitude. Substituting these functions and the forcing function, Eq. (5), into the equation of motion, Eq. (4), results in the following relationship:

$$F_o e^{i(2\pi ft)} = (-m(2\pi f)^2 + ib2\pi f + k)Xe^{i(2\pi ft)} \quad (7a\text{-}7c)$$

$$X = \frac{F_o}{(-m(2\pi f)^2 + ib2\pi f + k)}$$

$$\frac{X}{A} = \frac{\omega_n^2}{(-(\omega)^2 + i2\zeta\omega_n\omega + \omega_n^2)}$$

Eq. (7c) is written as the frequency response function relating the output to input ratio as a function of system characteristics, using $F_o = Ak$ (amplitude multiplied by stiffness) and the following natural frequency and viscous damping relationships:

$$\zeta = \frac{b}{2\sqrt{km}} \quad (8a\text{-}8b)$$

$$\omega_n = \sqrt{\frac{k}{m}}$$

Inserting X back into the equation for x(t), Eq. (6a), yields the following relationship:

$$x_p(t) = \frac{A}{1 - \left(\frac{\omega}{\omega_n}\right)^2 + i2\zeta\frac{\omega}{\omega_n}} e^{i(\omega t)} \quad (9)$$

Then, by expressing the system response in polar form, it is possible to compute the magnitude and phase of the frequency response function using Eq. (7c), yielding the following:

$$x_p(t) = \frac{F_o/k}{\sqrt{\left(1 - \left(\frac{\omega}{\omega_n}\right)^2\right)^2 + \left(2\zeta\frac{\omega}{\omega_n}\right)^2}} e^{i(\omega t - \phi)} \quad (10a\text{-}b)$$

$$\phi = \tan^{-1}\left(\frac{2\zeta\frac{\omega}{\omega_n}}{1 - \left(\frac{\omega}{\omega_n}\right)^2}\right)$$

Note that Eqs. (10a-b) imply that a linear time invariant system will produce an output that oscillates with the same frequency as the input, with a magnitude and frequency that is dependent on the input frequency and natural frequency of the system.

Exciting a system with an impulse excites the resonant frequencies of the system. This result can be understood by taking the Fourier transform of the impulse function, known as the Dirac delta. The Fourier transform of this impulse is a flat frequency response, and incorporates all of the information of the system in the impulse response when applied to a system. Starting with Eq. (4) and allowing the forcing function to be an impulse response, the solution for Eq. (4) becomes:

$$x(t) = \left[\frac{\dot{x}_o}{\omega_d}\sin(\omega_d t) + x_o\cos(\omega_d t)\right]e^{-\zeta\omega_n t} + \frac{F}{m\omega_d}e^{-\zeta\omega_n t}\sin(\omega_d t) \quad (11)$$

With the initial conditions of position and velocity set to zero, Eq. (11) reduces to:

$$x(t) = \frac{F}{m\omega_d}e^{-\zeta\omega_n t}\sin(\omega_d t) \quad (12)$$

Note that Eq. (12) indicates that a Fourier transform of the system will depict the damped natural frequency.

Vibrometry and Nonlinearity

A defect, fracture, or free floating mass violates the linearity assumptions in the basic vibrometry model, effectively changing the driving function. Such defect crack planes within the system can cause internal boundaries that act asymmetrically to a load, as the load is transferred through the crack from an input plane to an output plane, as indicated in the following equation:

$$m\ddot{x}(t) + b\dot{x}(t) + kH(x(t))x(t) = f(x_s + F_o \sin 2\pi ft - x) \quad (13)$$

This nonlinear response seen from the output crack plane side is a result of the initial displacement $x_s$ between the input and output crack planes, affecting the forcing function, and the separation of these planes is indicated in the stiffness term, by the presence of a Heaviside step function. Also present is a static load pressing the contact surfaces together. A shear load will cause friction as the surfaces rub against each other, while a perpendicular load will open the interface via tensile forces, which causes a discontinuity in the stiffness, even though the bulk material properties are normal under compression. These surfaces can also exhibit a short range adhesion force, or the surface contact can be under a static load, which will prevent the occurrence of a crack discontinuity, until the input force is such that the tensile loading cycle will surpass this crack adhesion. This gives rise to a threshold level of excitation that is needed to produce vibro-impact, or periodic impact of two rigid surfaces, which results in higher harmonic excitation.

Collecting Ultrasound Vibrometry Data from a Phantom

A series of experiments were performed to validate the operational principles illustrated in the configuration of FIG. 1, and to determine the type of equipment required to implement the ultrasound vibrometry methodology. Initially, an ultrasound phantom was constructed in order to simulate the mechanics of a loose or fixated arthroplasty system.

FIG. 5 schematically illustrates the ultrasound phantom constructed in order to simulate the mechanics of a loose or fixated medical implant system, including two acrylic masses, simulating bone and the implant, positioned as a two-degree of freedom mass-spring-damper system, with hard contacts. Mass 42 simulated bone, while mass 44 simulated the implant. The system could be adjusted by drawing the two masses together by tightening a screw (not shown)

extending through mass 42. This system was driven at various frequencies by an electromagnetic actuator 40 (SA-1™, CSA Engineering). Actuator 40 was powered by a Wavetek model 19™ (Wavetek, London, UK) function generator amplified using an Aura Interactor sound amplifier. The masses in the system were tested suspended in a water bath 46. An accelerometer 48 (Microtron™, available from Endevco, San Juan Capistrano, Calif.) was used to compare system output to that measured by ultrasound probe 20.

In a first study, ultrasound probe 20 was implemented using a Transpect™ Doppler ultrasound machine (Transpect TCD™, Medasonics, Fremont, Calif.). The ultrasound was positioned in the water of the tank, with the sampling gate of the ultrasound system measuring vibration information from various areas of the system. The data were collected through the audio outputs of the ultrasound system and acquired using a portable National Instruments™ USB DAQ board and Lab-VIEW™ (National Instruments, Austin, Tex.).

The phantom system was driven with sinusoidal frequencies sweeping from 80-500 Hz. The natural (resonant) frequencies of the system were determined from the amplitude versus frequency graph. At these resonant frequencies, the two masses were tightened together in increments, and the output waveforms were measured, until the masses were locked together, effectively forming one mass.

Initially, there was difficulty obtaining a clear reading from the probe unless it was oriented at an extreme angle away from the axis of vibration. This observation was found to be the result of the intense reflections caused by the acrylic and metal materials constituting the phantom. The strong signal magnitudes were truncated by the Doppler system, causing a clipping effect graphically illustrated in FIG. 6, which graphically illustrates the time amplitude relationship for the phantom of FIG. 5, as measured for comparison, using an accelerometer and ultrasound probe.

FIG. 7A graphically illustrates the power and frequency spectrum of the phantom of FIG. 5 in a loose configuration, with the ultrasound probe being gated on the phantom. FIG. 7B graphically illustrates the power and frequency spectrum of the phantom of FIG. 5 in a loose configuration, with the ultrasound probe being gated off the phantom. FIG. 8 graphically illustrates the power and frequency spectrum of the phantom of FIG. 5 in a tight configuration, with the ultrasound probe being gated off the phantom.

The artifact of FIG. 6 was verified to be a clipping effect (as opposed to being a non-linear output) by testing the tight phantom while increasing the signal strength. It became obvious that the internal circuitry of the ultrasound unit was saturated at an amplitude of 1.5, with a clean cut-off of the sinusoidal wave. Signal strength was adjusted by moving the gate (or recording) depth of the Doppler sampling area off of the surface of the phantom. This change caused a low-pass filtering effect due to the dampening properties of the surrounding liquid. This phenomenon is illustrated in FIGS. 7A and 7B, which graphically show the harmonics of a loose system changed due to gating depth. It was determined that this clipping effect would not present a problem for an in vivo system, due to the natural dissipation of the vibrational signal in the surrounding tissues. FIGS. 7A and 7B indicate that correct gate position is important, due to the possibility of signal attenuation in surrounding tissues.

Another artifact of the Transpect Doppler system was its tendency to filter signals below about 120 Hz. This characteristic is a feature of most Doppler systems meant to decrease the signal caused by the movement of surrounding vascular walls and tissues when blood velocity is measured. This filter can be eliminated from the data collected by many ultrasound units, such as the Sonosite™ Doppler ultrasound system, which offers the ability to collect data directly from the transmitter.

Note that FIGS. 7A, 7B, and 8 clearly show that ultrasound can detect dynamic positioning of the phantom masses (see FIG. 5) sufficiently well to differentiate a tight configuration of the two masses from a loose configuration of the two masses. This effect can be seen from the presence of harmonics and extraneous frequency components due to the non-linear contact vibration of a loose second mass in the system.
Collecting Ultrasound Vibrometry Data from a Patient's Ankle without an Implant Additional testing was performed using two volunteers to determine if the electromagnetic actuator (vibration source 16 of FIGS. 1 and 2) could indeed vibrate the bones of the foot. The experimental set up for the first volunteer required the test subject to sit in a chair, with a leg resting on a foam support. The actuator and an accelerometer were attached to the midpoint of an acrylic bar measuring 3 mm×1.5 mm×25 mm. On the opposite side of the bar, a polyurethane heel cup was attached at the midpoint. The cup was placed onto the right heel of the subject, and hook and loop fasteners were used on the ends of the acrylic bar to firmly attach the heel cup against the calcaneus. The hook and loop fasteners wrapped around the shin and distal end of the foot, maintaining the foot in plantar flexion. The transducer of the Transpect Doppler ultrasound unit was attached to an adjustable clamp, which was in turn, attached to a heavy steel fixture placed on the floor. This arrangement mechanically substantially insulated the transducer from the vibration. The transducer was pointed at the talus from the dorsal aspect of the foot. Liberal amounts of ultrasound gel were used to prevent the face of the transducer from coming into contact with the skin of the foot.

One problem that presented itself immediately was the proximity of the transducer to the talus. This configuration was a problem because the Transpect Doppler ultrasound machine being used had a minimum gate area of 25 mm, which was deeper than that of the talar surface. Though the vibration of the bone was being read due to the penetrating characteristics of the 2 MHz probe, there was a concern that reflections that had been bounced repeatedly were also being read. A possible solution would have been to use a gel stand-off to distance the transducer from the ankle. However, another available ultrasound unit (the Sonosite Doppler ultrasound unit) was used instead, because the Sonosite Doppler ultrasound unit could be set to a much shallower gate depth. A frequency sweep of the ankles from 80 Hz to 500 Hz showed two resonant peaks in one subject and one peak in the other subject (see FIGS. 9, 10, and 11).

FIG. 9 graphically illustrates a comparison of the amplitude and frequency spectrum of a first patient's ankle undergoing induced vibration collected using both an accelerometer and an ultrasound probe. FIG. 10 graphically illustrates the power and frequency spectrum of a first patient's ankle undergoing induced vibration collected using an ultrasound probe, and FIG. 11 graphically illustrates the power and frequency spectrum of a second patient's ankle undergoing induced vibration collected using an ultrasound probe. Note that the absence of a second peak in the second subject (se FIG. 11) is likely due to the 130 Hz cut-off range of the Sonosite ultrasound unit. Referring to FIG. 9, the spectrum of the Doppler ultrasound output was compared to the spectrum of the accelerometer to determine if the frequency measurement was preserved.

FIG. 12 graphically illustrates the power and frequency spectrum of a first patient's ankle undergoing induced vibration collected using both an accelerometer and ultrasound probe, showing that Doppler ultrasound is able to read the frequency of the actuator's driving force.

Throughout the testing, some clipping in the Transpect Doppler signal was detected. However, it was determined that by changing the Pulse Repetition Frequency (PRF), the clipping subsided. This result is likely caused by different circuitry being used for higher PRFs. While not tested, it is likely that a higher PRF, along with a gel standoff would alleviate the clipping effect in this particular Transpect Doppler ultrasound unit. This embodiment was not tested because an alternate ultrasound unit (the Sonosite ultrasound unit) did not suffer from such clipping.

The actuator used in the experiments was being driven near its peak force output capacity. A larger actuator would provide increased force output, if needed to surpass the threshold required to activate vibro impact in a loose implant, yet would permit the power level to be turned down, as desired.

Additional data were collected for the second test subject using the ultrasound unit that did not exhibit the clipping issue. The additional ultrasound data for the second test subject was acquired using a Sonosite Micromax™ Doppler ultrasound system (SonoSite Inc, Bothell, Wash.). Data were collected using a USB docking station and a MATLAB™ (The MathWorks Inc. Natick, Mass.) script. The transducer of the Sonosite Doppler ultrasound was held by an assistant to the ankle. The transducer was pointed at the talus from the dorsal aspect of the foot. Liberal amounts of ultrasound gel were used to prevent the face of the transducer from coming into contact with the skin of the foot, preventing vibration of the transducer. The PRF of the Doppler ultrasound was set to 1563 Hz, the size of the sampling gate was set to 3 mm, and the frequency was swept from 150 Hz to 400 Hz in increments of 50 Hz.

One limitation with the MATLAB acquisition software was that it would only record 1024 data points at a time with the sample rate equal to the PRF. This limitation did not enable continuous data collection; therefore, the driving frequency had to be set incrementally before acquiring data. While this data set did indicate that it was possible to collect useful data while holding the ultrasound probe by hand, doing so introduced a large low-frequency component to the data corresponding to the hand movement of the person holding the probe. Thus, holding the probe in a fixed position using a frame would eliminate this component.

FIG. 13 graphically illustrates the power and frequency spectrum of the second patient's ankle undergoing induced vibration collected using ultrasound while sweeping through a plurality of frequencies. Note the data for FIG. 13 were collected with the Sonosite unit. The Sonosite system alleviates problems inherent in the Transpect Doppler system, such as clipping, low pass wall filtering, and minimum sampling gate depth, though data acquisition was limited to 1024 points by the custom software.

These tests on normal ankles (no implant) show that ultrasound was able to obtain vibrational information in an in-vivo situation. These tests suggested that while free hand ultrasound probes could be used to collect useful data, ultrasound probes mounted in a fixed position enable higher quality data to be acquired.

Collecting Ultrasound Vibrometry Data from a Cadaver with an Ankle Implant

To determine if ultrasound could indeed collected data that can be used to evaluate the degree of tightness (i.e., osteointegration) of an implant, cadaveric testing was implemented.

Two matched 67 year-old male cadaveric ankles were implanted with size 4 Agility™ total ankle systems with augmented talus components. These components were explanted prosthetics obtained from revision surgeries. A single surgeon implanted both prosthetics into the cadaveric specimens. The tibial component in each specimen was cemented to the tibia and fibula to simulate solid osteointegration. The talar component for one ankle specimen was press fit into the talus to simulate a loose implant. The talar component for the other ankle was cemented into the talus using bone cement to simulate full osteointegration.

For the ultrasound vibrometry testing, each cadaveric ankle specimen was filled with ultrasonic transmission gel (Aquasonic 100™, Parker Laboratories, Fairfield, Va.). This step was carried out because the surgery created a large wound anteriorly in each specimen. This wound included interstitial air due to the lack of blood flow. The ultrasound transmission gel was used to displace the air and allow the ultrasound to be coupled to the implant with minimal impedance from air pockets. The specimens were then attached to a custom ankle-foot orthoses (AFO) that included the electromagnetic actuator (generally described above with respect to the normal ankle testing). The AFO construct was then suspended to ensure vibrational isolation of the construct. The Sonosite Doppler ultrasound probe was fixed, positioned anterior to the ankle.

By observing the Fourier spectrum of the vibrational output, it was determined that the implant constructs represent non-linear systems due to the presence of harmonics. These harmonics were more prevalent at lower driving frequencies, which was possibly due to the increased energy input at these driving frequencies.

FIG. 14A graphically illustrates the normalized power and frequency spectrum of a loose cadaver implant undergoing induced vibration, where the data are collected using ultrasound, and FIG. 14B graphically illustrates the normalized power and frequency spectrum of a tight cadaver implant undergoing induced vibration, where the data are collected using the ultrasound probe.

To quantify the amount of non-linearity, and therefore osteointegration, magnitude ratios of the primary frequency component and the harmonics were computed (Table 1, see below). The ratios become smaller for comparatively smaller harmonics, denoting a more integrated, linear system. These ratios alone were not useful at higher frequencies, because the smaller output produced significant looking ratios with what appears to be the noise floor. It is therefore of interest to use lower frequency data as well as the manual observation of harmonic frequencies above the noise floor for interpretation of osteointegration. These findings suggest that the ultrasonic vibrometry can ascertain the difference between loose and tight implants, although it appears that the sensitivity doesn't seem to be very high. This limitation could be an aspect of the cadaveric model used, since the "loose" implant was press fit snugly into the talus, and the freshly cut cancellous bone seemed to grip the porous coating of the implant with a high affinity.

FIG. 15A graphically illustrates a complex time history of ultrasound data collected from a loose cadaver implant undergoing induced vibration, while FIG. 15B graphically illustrates a complex time history of ultrasound data collected from a tight cadaver implant undergoing induced vibration.

TABLE 1

Magnitude ratios of secondary harmonic to primary frequency component.

| Driving Frequency | | Loose | Tight |
|---|---|---|---|
| 78 | $1^{st}$ | 0.015 | 0.006 |
| | $2^{nd}$ | 0.020 | 0.007 |
| | $3^{rd}$ | 0.046 | 0.005 |
| 100 | $1^{st}$ | 0.015 | 0.015 |
| | $2^{nd}$ | 0.044 | 0.002 |
| | $3^{rd}$ | 0.002 | 0.003 |

TABLE 1-continued

Magnitude ratios of secondary harmonic
to primary frequency component.

| Driving Frequency | | Loose | Tight |
|---|---|---|---|
| 150 | $1^{st}$ | 0.124 | 0.010 |
|  | $2^{nd}$ | 0.034 | 0.004 |
|  | $3^{rd}$ | 0.017 | 0.005 |
| 200 |  | 0.002 | 0.001 |
| 250 |  | 0.012 | 0.001 |
| 300 |  | 0.022 | 0.008 |

A lower ratio represents a tighter prosthesis.

The cadaveric ultrasound ankle implant study indicates that ultrasound vibrometry can distinguish between loose and tight cadaveric implants at low frequencies, although it was noted that multiple samples should be obtained. High frequencies had a smaller signal-to-noise ratio and therefore, were unreliable. It was further noted that the difference between the cadaveric specimen fixations might have been smaller than intended, which would have increased the difficulty in observing a distinction.

Collecting Laser Vibrometry Data from a Model with an Ankle Implant

A laser vibrometry data study was performed to determine if laser vibrometry could be similarly employed to collect data that could be used to evaluate the degree of osteointegration of an implant. While laser vibrometry can only be used during an operative procedure for an internal implant, collecting such data during operative procedures could be useful in its own right, and also can be used to acquire a data set for calibrating ultrasound data collected non-invasively. The laser vibrometry experiments were performed to determine the relationship between the impulse testing spectrum and implant fixation using laser vibrometry.

A bench top model was constructed to simulate the progressive osteointegration of a talar component. Agility Total Ankle™ explants were obtained and implanted into solid rigid polyurethane foam (Sawbones, Pacific Research Laboratories, Vashon, Wash.). A prototype cantilever with a reflective tape surface (3M, St. Paul, Minn.) was inserted into the threaded hole present in the talar components. These constructs were then laterally compressed using an angle vice to a series of torques measured with a torque wrench. These torques controlled the amount the bone foam laterally gripping the talar component, representing a range of fixations. The constructs were struck with an impactor pen at each different torque setting, and the resulting vibrations measured using a laser Doppler vibrometer (Polytec OFV 3000™ Controller with OFV 302™ Sensor Head, GmbH, Waldbronn, Germany). Based on theory, it was expected that the output spectrum would indicate a higher clamping condition (and therefore fixation) through an increase in peak harmonic frequency.

FIG. 16 graphically illustrates the power and frequency spectrum of a model ankle implant undergoing induced vibration, where the data are collected using laser vibrometry at a plurality of different model torque settings. FIG. 17A graphically illustrates the power and frequency spectrum of the model ankle implant undergoing induced vibration, where the data are collected using laser vibrometry at a first model torque setting, while FIG. 17B graphically illustrates the power and frequency spectrum of the model ankle implant undergoing induced vibration, where the data are collected using laser vibrometry at a second model torque setting.

FIG. 18 graphically illustrates the torque and frequency spectrum of a model ankle implant undergoing induced vibration, where the data are collected using laser vibrometry at a plurality of different model torque settings. By marking the frequencies of the resonant peaks that were generated, a graph of these peaks versus the torques at which they were created was constructed, as shown in FIG. 18, depicting how the system resonance changes. The data collected in this study indicate that laser Doppler vibrometer can distinguish between loose and tight (i.e., osteointegrated) talar implants based upon a torque osteointegration model.

Another bench top model was constructed to simulate the osteointegration of a talar component. Again, Agility Total Ankle™ explants were obtained and implanted into solid rigid polyurethane foam (Sawbones™, Pacific Research Laboratories, Vashon, Wash.). A cantilever with a reflective tape surface was inserted into the threaded hole present in the talar components. In this test, polymethylmethacrylate (PMMA) was used to simulate osteointegration of the implant. PMMA was placed between the implant and sawbone foam interface and allowed to cure. The constructs were struck with an impact pen at various times during the curing period, representing different amounts of osteointegration of the implant. The resulting vibrations were measured using a laser Doppler vibrometer.

FIG. 19 graphically illustrates the power and frequency spectrum of a second exemplary model ankle implant undergoing induced vibration, where the data are collected using laser vibrometry during various cement cure times. FIG. 20 graphically illustrates the time and frequency spectrum of the second exemplary model ankle implant undergoing induced vibration, where the data are collected using laser vibrometry, during various cure times.

Note that FIG. 20 was generated by marking the frequencies of the resonant peaks that were generated, yielding a graph of these peaks versus the cement curing times at which they were created, to depict how the system changes resonance. Since cement is commonly used to affix an implant into bone, it was assumed that a cemented implant that was cured would approximate a fully osteointegrated implant, and various stages of cement curing would give a gradation of osteointegration as well. This data represents the ability of the laser Doppler vibrometer to distinguish between osteointegrated talar implants based upon a cement osteointegration model.

The laser vibrometry technique was also tested for sensitivity to angle, type of impactor pen, and talar component strike area. In the test for angle sensitivity, the implant was set up in a foam construct at a torque of 20 ft/lbs, using the cantilever for the laser reflection surface. The spectrum was measured and plotted versus the angle of the laser to the cantilever, providing the graph of FIG. 21, which illustrates the power and frequency spectrum of the second exemplary model ankle implant undergoing induced vibration, for data collected using laser vibrometry at various laser incidence angles. Three impactor pens were constructed of slightly varying size. FIG. 39 illustrates an exemplary impactor pen. FIG. 40 schematically illustrates an exemplary impact pen 402 in contact with an implant 404 via a surgical wound 406. FIG. 22 graphically illustrates the power and frequency spectrum of the second exemplary model ankle implant undergoing induced vibration, where the data are collected using laser vibrometry, and three different impact sources are used.

In addition to using different impact sources, different portions of the model (i.e., different strike zones) were also tested. FIG. 23 graphically illustrates the power and frequency spectrum of the second exemplary model ankle implant undergoing induced vibration, where the data are collected using laser vibrometry, and different portions of the model are struck to induce the vibration.

With respect to the angle sensitivity tests, it was determined that only the magnitude of the signal changed with laser incidence angle. Because the desired parameter is the frequency response, the magnitude dependence on the incidence angle should not be an issue, so long as the angle is not extreme.

With respect to different impactor pen tests, it was determined that only the magnitude of the signal changed with impactor pen size. Again, because the desired parameter is the frequency response; the magnitude dependence on impactor pen type should not be an issue. Smaller magnitude responses are likely to be less desirable; thus, impactors generating larger responses are likely to be preferred.

With respect to tests of the strike area sensitivity, it was determined that the primary effect of strike placement was a change in the signal magnitude, although there was some variation in secondary resonance peaks. Once again, because the desired parameter is the frequency response, the magnitude dependence on strike area should not be much of a concern, although in practice, an attempt should be made to repeatably strike the same area of the implant during testing.

In the laser vibrometry testing, the spectrum peaks of the talar component were found to increase in frequency as a function of both clamping force and cement curing time. Therefore, increased spectrum peak frequencies are indicative of osteointegration, based on the approximations used to simulate a fixed implant. It was also determined that the angle of the laser incidence on the reflection area primarily affects signal magnitude, not signal frequency. The impactor pen tests demonstrated that different impactors also primarily affect signal magnitude, not signal frequency. Finally, an analysis of the strike area showed that variations in strike area did not have an extreme impact on the output frequency response (although in practice, it is preferable to strike the same location on the implant).

Collecting Laser Vibrometry Data from a Cadaver with an Ankle Implant

The two matched cadaveric specimens discussed above were also tested with the laser Doppler vibrometer. Each was mounted with a prototype cantilever incorporating reflective tape. The implant specimens (one loose and one tight) were tested once in a relaxed configuration, and then again, with adjacent skin retracted to ensure no tissue interfered with the measurement. In each test, the talar component of the implant was struck with an impactor pen, and the resulting vibration was measured with the laser vibrometer.

FIG. 24 graphically illustrates the power and frequency spectrum of a loose ankle implant in a cadaver undergoing induced vibration, where the data are collected using laser vibrometry. FIG. 25 graphically illustrates the power and frequency spectrum of a tight ankle implant in a cadaver undergoing induced vibration, where the data are collected using laser vibrometry. The spectra for both the loose and the tight specimens demonstrated two resonant peaks. The peaks whose frequencies were around 2 KHz had a larger magnitude than peaks of lower or higher frequencies. The peak numbers and their values can be found in Table 2.

TABLE 2

Resonant peak frequencies of loose and tight cadaveric testing.

| | Implant | | | |
|---|---|---|---|---|
| | Loose Implant | | Tight Implant | |
| Configuration | Relaxed | Retracted | Relaxed | Retracted |
| First Peak | 814 Hz | 824 Hz | 2343 Hz | 3002 Hz |
| Second Peak | 1613 Hz | 1993 Hz | 5457 Hz | 4309 Hz |

It can be seen that the tight implant construct has resonant peaks that have higher frequencies than the loose implant, as well as an increasing frequency for the peak with the higher magnitude. This phenomenon could be due to the implant vibrating at different modes, which may increase the magnitude with respect to other modes as the implant becomes more tightly bonded with the talus.

The frequencies seen in the laser testing results show the differences in tightness between the loose and tight cadaveric constructs were not as large as was assumed. The "loose" construct was actually quite tightly press fit onto the talus, and may not have provided the large fixation range that was desired. Even with the relative small fixation range between the loose and tight cadaver implants, laser vibrometry was able to distinguish between the loose and tight cadaver implants.

Preliminary Study Conclusions

Based on the preliminary studies discussed above, the following conclusions were formed: (1) Ultrasound Vibrometry can distinguish between a loose and tight model system; (2) Ultrasound Vibrometry can obtain vibrational data in vivo; (3) Ultrasound Vibrometry can distinguish between fixation in vitro; (4) Laser Vibrometry can measure fixation in a model system; (5) Laser Vibrometry is robust with respect to strike placement, magnitude, and laser angle; and (6) Laser Vibrometry can distinguish between fixation in vitro.

Clinical Research

The following clinical study was implemented to determine if it was possible to predict and quantify a loose talar implant using non-invasive ultrasound vibrometry in a clinical setting, using consenting patients. The study examined the efficacy of laser Doppler vibrometry as a method to intraoperatively quantify osteointegration, as well as to validate the ultrasound vibrometry observations obtained in the clinical setting. By investigating the statistical relationship between ultrasound data and physician score at the same time as laser data and physician score, a more direct quantitative relationship can be directly determined between ultrasound data and laser data. For example, FIG. 26 schematically illustrates a regression comparison between three different techniques used to evaluate the degree of osteointegration of an implant, using non-invasive ultrasound vibrometry, inter-operational laser vibrometry, and inter-operational physician scoring.

Patients who were scheduled for a revision surgery to replace part or all of the Agility Total Ankle™ prosthesis were contacted by their physician to determine if they were willing to participate in the study. Patient exclusion criteria excluded those with hypersensitivity, such as fibromyalgia, or those who have already had a stemmed prosthesis in place. Patients were tested in the clinic when they visited for their preoperative exams. The testing in the clinic was done using the ultrasound and electromagnetic actuator system described above (i.e., FIGS. 1 and 2). The number of patients enrolled in the study was 20, resulting in 18 usable data sets.

During the preoperative clinical visit, patients were taken to an exam room and the study procedure was explained to them. The patient was then positioned comfortably on a bed or a chair with the prosthetic incorporating leg resting on a foam support. The foam support contacted the leg at the upper calf, so that the foot, ankle, and part of the lower leg hung suspended in the air. This configuration provided mechanical isolation, so that the ankle was allowed to vibrate freely. The ankle was then attached to the custom AFO incorporating the electromagnetic actuator. This AFO positioned the ankle in plantar flexion to rotate the talar component toward the anterior of the ankle. The probe from the Doppler ultrasound machine was then suspended above the ankle while fixed to a separate clamp. This configuration provided the ultrasound probe vibrational isolation from the actuator. The probe was then put into contact with the ankle using copious amounts of ultrasonic transmission gel, which further isolated vibration but provided signal transmission to the probe.

The primary data input setting was kept constant (approximately 1 g at 100 Hz) for all patients, though the actual output amplitude of the actuator changed according to frequency. After the initial preliminary patients were tested, additional data were acquired at approximately 0.5 and 1.5 g input amplitude settings at 100 Hz. The amplitude values of 0.5 g, 1 g, and 1.5 g respectively corresponded to input settings 5, 6, and 7 on the Aura™ amplifier. The additional data were collected for only 11 of the patients, so the primary 1 g 100 Hz data were down-sampled during comparisons to the other amplitude data. This step was done to analyze the effect of input amplitude on the vibro impact threshold, and to explore the driving amplitude relationship to signal-to-noise ratio.

The patients' implanted ankles were vibrated at frequencies ranging from 100-200 Hz, in increments of 50 Hz, although the preliminary testing discussed above suggested that the 100 Hz data were optimal. For data collection, the ultrasound unit was operated in Doppler mode, which allowed a 3 mm sampling volume to be targeted at the surface of the talar component, as seen in the ultrasound display. The sampling rate was set to 1563 Hz, and 1024 samples of data were collected per recording incident. Data were collected three times at each frequency level, for noise averaging.

The vibrometry data from the ultrasound were analyzed using MATLAB™. Fourier transforms of the data were obtained, and a metric based upon the ratio of harmonics observed (similar to the cadaveric ultrasound study) was created to correlate the clinical data to the surgical data. Exemplary ultrasound data analysis involved identifying a magnitude ratio of the second harmonic component to the driving frequency. This ratio was the primary ultrasound metric used to identify the osteointegration of the subject clinically.

Table 3 (below) includes data collected in the clinical setting using ultrasound vibrometry. Some data sets in Table 3 are incomplete, due to data acquisition procedures that were changed after preliminary data analysis.

Inter-Operative Research

Inter-operative laser vibrometry studies were also performed on the same patients involved in the clinical ultrasound vibrometry study. The patients were tested during surgery using the laser Doppler vibrometer, prior to the extraction of the prosthesis. During these studies, the laser unit was disposed in the operating theater in line of sight of the operating site, but out of the physician's way. The laser unit was mounted to a boom away from and above the patient, although many other locations can be employed.

In order to provide a repeatable impulse to the talar component inter-operatively, an impactor pen was developed. This instrument was constructed so that the physician could deliver a repeatable strike to the implant in-vivo. The pen was fabricated out of acrylic and polycarbonate for ease of use, and so that it would not damage the implant if the talar component was kept in the patient. It was also constructed to be as silent as possible so that it could be used in conjunction with acoustical methods of vibrometry.

In order to provide a consistent reflective surface that does not affect the talar component, it was necessary to construct a cantilever that attached to the component and projected the reflective surface out of the wound. A cylinder with a threaded end was machined to interface with the threaded assembly already present in the talar components. Reflective bead tape (Scotchlite 8726, 3M, St. Paul, Minn.) was attached to the top of the cantilever to efficiently scatter the reflected laser light back to the receiver. FIG. 27 schematically illustrates a cantilever 200 with a machined head 202 added to a medical implant 204 to facilitate laser vibrometry.

TABLE 3

Ultrasound clinic data. Values for the ultrasound at various driving frequencies are the ratio of the second harmonic to the primary harmonic. The first harmonic represents the power of the primary harmonic for a 100 Hz driving frequency, as recorded by the ultrasound probe.

| Patient | Physician Score | 100 Hz (Primary) | 100 Hz-1.5 g | 100 Hz-1 g | 100 Hz-0.5 g | 150 Hz | 200 Hz | $1^{st}$ Harmonic |
|---|---|---|---|---|---|---|---|---|
| 1 | 1 | 0.00148 | 0.01160 | 0.00148 | 0.00057 | 0.00041 | 0.00600 | 0.281 |
| 2 | 1 | 0.00062 | 0.00492 | 0.00062 | 0.00016 | 0.00100 | 0.00080 | 0.713 |
| 3 | 2 | 0.00165 | | | | 0.00004 | 0.00096 | 1.33 |
| 4 | 2 | 0.01634 | | | | 0.00011 | 0.00050 | 2.66 |
| 5 | 2 | 0.00124 | | | | 0.00045 | 0.00150 | 0.491 |
| 6 | 3 | 0.00068 | | | | 0.00021 | 0.00314 | 3.91 |
| 7 | 3 | 0.00038 | | | | 0.00059 | 0.00140 | 0.63 |
| 8 | 3 | 0.00025 | 0.00190 | 0.00025 | 0.00025 | 0.00079 | 0.00110 | 0.26 |
| 9 | 3 | 0.00043 | 0.00280 | 0.00043 | 0.00015 | 0.00088 | 0.00355 | 0.21 |
| 10 | 3 | 0.00134 | 0.00104 | 0.00134 | 0.00051 | 0.00004 | 0.00325 | 0.846 |
| 11 | 4 | 0.00013 | | | | 0.00078 | 0.00400 | 0.75 |
| 12 | 4 | 0.00030 | 0.00077 | 0.00030 | 0.00003 | 0.00012 | 0.00013 | 3.66 |
| 13 | 4 | 0.00160 | 0.00254 | 0.00160 | 0.00005 | 0.00045 | 0.00014 | 3.92 |
| 14 | 5 | 0.00011 | 0.00110 | 0.00011 | 0.00013 | 0.00014 | 0.00032 | 0.784 |
| 15 | 5 | 0.00033 | 0.00047 | 0.00033 | 0.00011 | 0.00014 | 0.00010 | 1.08 |
| 16 | 5 | 0.00010 | | | | 0.00001 | 0.00077 | 1.33 |
| 17 | 5 | 0.00010 | 0.00117 | 0.00010 | 0.00002 | 0.00002 | 0.00015 | 1.28 |
| 18 | 5 | 0.00009 | 0.00101 | 0.00009 | 0.00085 | 0.00032 | 0.00200 | 0.477 |

The laser Doppler vibrometry was performed during the patient's revision surgery. Each patient had a surgical incision opened on the anterior of the ankle down to the mortise joint, as is standard for a total ankle revision. Any heterotopic bone formation obstructing the anterior surface of the talar component was removed and the threaded hole in the component cleared of debris. The machined cantilever with reflective bead tape on the end surface was attached to this threaded hole, using a nut driver turned to hand tightness. The foot was stabilized and the sides of the wound slightly retracted to un-encumber the cantilever. The laser vibrometer was placed on a boom stand to keep it clear of the surgical field, yet allow it to have a clear path to the cantilever.

The lens of the laser vibrometer was opened at full f-stop and focused on the top of the cantilever. The talar component was then impacted with the custom impactor pen on the anterolateral surface by the physician. The data from the laser vibrometer were read at a 20 KHz sampling rate using a USB data acquisition card to LABVIEW™. The implant was impacted multiple times to ensure a reading and for noise averaging. The cantilever was then removed and the standard handle placed in the talar component's threaded hole (incorporated into the device for a handle). The surgeon then gave a measurement of stability based on the following criteria (Table 4).

TABLE 4

Physician intra-operative grading criteria for talar component osteointegration.

| Physician Osteo-integration Score | Criteria |
|---|---|
| 1 | Completely loose, can be removed without tools. |
| 2 | Very loose, attached with soft tissue or minimal bone. |
| 3 | Slight movement between talus and implant, some attachment of bone. |
| 4 | No discernable movement between talus and implant but noticeable fluid flux from interface between the two. |
| 5 | Solidly bonded prosthesis. |

The vibrometry data from the laser was analyzed using MATLAB™. Fourier transforms of the data were obtained and a metric based upon the frequency of signal components observed (similar to the cadaveric laser study) was created to correlate the clinical data to the surgical data. The laser vibrometry analysis was based upon the frequency values of the prominent resonant peaks of the laser vibrometry data, and these data were used as the primary metric to determine the osteointegration of the subject inter-operatively.

Table 5 includes both physician scoring data and laser vibrometry data collected inter-operatively for each patient in the study. Some data sets in Table 5 are incomplete due to unusable data from difficulties experienced in collecting the data inter-operatively.

TABLE 5

Inter-operative Laser Vibrometry Data.

| Patient | Physician Score | Laser Peak Hz |
|---|---|---|
| 1 | 1 | 566 |
| 2 | 1 | 449 |
| 3 | 2 | |
| 4 | 2 | |
| 5 | 2 | 1309 |
| 6 | 3 | |
| 7 | 3 | 976 |
| 8 | 3 | 703 |
| 9 | 3 | |
| 10 | 3 | 957 |
| 11 | 4 | 1602 |
| 12 | 4 | 2754 |
| 13 | 4 | |
| 14 | 5 | 2285 |
| 15 | 5 | 2031 |
| 16 | 5 | |
| 17 | 5 | 2813 |
| 18 | 5 | |

Values for laser constitute the frequency of the prominent harmonic peak.

Data Analysis and Statistical Modeling

To increase the effectiveness of the techniques disclosed herein to quantify osteointegration in total ankle arthroplasty, the metric obtained clinically should be mapped theoretically to a preferred measurement of osteointegration, for example, by constructing a model representing the statistical relationship between two sets of empirical data, one corresponding to the clinical metric, and the other relating to implant osteointegration.

Also analyzed were various patient characteristics and other metrics of interest to determine what, if any, effect they might have upon osteointegration. These metrics were collected based on the preliminary analysis (such as implant size, length of implantation, age, and gender), observed issues during the surgery (such as cysts and the presence of poly-wear), and simple curiosity (regarding the physician's ability to estimate looseness). These characteristics and metrics are summarized in Table 6.

Data from the ultrasound and the laser were both initially analyzed for correlation to the physician score metric using the non-parametric association of Spearman's Rho. Then a regression model for both the ultrasound and laser data sets versus the physicians score data was constructed using ordinal logistic regression. Finally, a nonlinear regression model was constructed between the ultrasound and laser data. All statistical analyses were performed using SPSS™ (Version 15.0, SPSS Inc., Chicago, Ill.).

To obtain a predictive model to determine osteointegration of the Agility™ talar component, a correlation was first performed to determine trends in the data. This correlation enabled more complex relationship models to later be developed. A correlation of the clinical and inter-operative fixation measurements to the osteointegration determined by the physician score is shown in Table 7. The relationships between the patient characteristics and osteointegration score were also characterized, as shown in Table 7.

TABLE 6

Patient characteristic data and other metrics of interest. Physician's estimation for revision values correspond to Loose (L) or Pain (P). Poly-wear values are 0, 1, and 2 for no wear, suspected front-side wear, and suspected backside wear respectively. Cyst values are 0 for no cysts and 1 for cysts present.

| Patient | Physician Score | Phys. Estimation | Size | Poly | Cyst | Age | Sex | Implant Time [wk] |
|---|---|---|---|---|---|---|---|---|
| 1 | 1 | L | 2 | 0 | 0 | 60 | f | 208 |
| 2 | 1 | L | 2 | 1 | 1 | 67 | m | 286 |
| 3 | 2 | L | 3 | 0 | 0 | 71 | f | 214 |
| 4 | 2 | L | 4 | 2 | 1 | 59 | m | 285 |
| 5 | 2 | L | 5 | 2 | 0 | 80 | m | 399 |
| 6 | 3 | P | 2 | 0 | 0 | 35 | f | 235 |
| 7 | 3 | P | 3 | 2 | 1 | 59 | f | 364 |
| 8 | 3 | P | 6 | 0 | 1 | 84 | m | 250 |
| 9 | 3 | L | 6 | 0 | 0 | 49 | m | 181 |
| 10 | 3 | L | 3 | 2 | 0 | 59 | f | 255 |
| 11 | 4 | L | 3 | 1 | 0 | 65 | f | 97 |
| 12 | 4 | L | 6 | 1 | 0 | 54 | m | 189 |
| 13 | 4 | P | 6 | 2 | 0 | 74 | m | 481 |
| 14 | 5 | P | 5 | 2 | 1 | 73 | m | 243 |
| 15 | 5 | L | 5 | 2 | 0 | 50 | m | 432 |
| 16 | 5 | | 3 | | | 68 | f | 37 |
| 17 | 5 | P | 4 | 2 | 0 | 43 | m | 315 |
| 18 | 5 | P | 3 | 1 | 0 | 42 | m | 555 |

TABLE 7

Spearman's Rho comparisons between physician's osteointegration score and test metrics from clinical testing, inter-operative testing, and patient characteristics.

| Physician's Osteointegration Score vs. | Spearman's Rho | Sig. (2-tailed) |
|---|---|---|
| Ultrasound 100 Hz Ratio (Primary) (n = 18) | −0.766 | 0.00021 |
| 1$^{st}$ Harmonic Amplitude (n = 18) | 0.200 | 0.426 |
| Ultrasound 100 Hz 1.5 g Ratio (n = 11) | −0.727 | 0.011 |
| Ultrasound 100 Hz 1 g Ratio (n = 11) | −0.670 | 0.024 |
| Ultrasound 100 Hz 0.5 g Ratio (n = 11) | −0.439 | 0.177 |
| Ultrasound 150 Hz Ratio (n = 18) | −0.344 | 0.162 |
| Ultrasound 200 Hz Ratio (n = 18) | −0.435 | 0.071 |
| Laser Peak Frequency (n = 11) | 0.916 | 0.00008 |
| Size (n = 18) | 0.361 | 0.140 |
| Age (n = 18) | −0.193 | 0.442 |
| Implant Time (n = 18) | 0.144 | 0.569 |
| Gender (n = 18) | 0.250 | 0.318 |
| Poly-wear (n = 17) | 0.292 | 0.240 |
| Presence of Cysts (n = 17) | −0.284 | 0.253 |
| Physician's Fixation Estimate (n = 17) | 0.567 | 0.018 |

It can be seen from the correlations of the ultrasound data to the physician's osteointegration score that the ratio of the second harmonic to the first harmonic for the 100 Hz driving frequency is well correlated with osteointegration. This phenomenon is also seen graphically on the scatter plot for this data (FIG. 28). To further analyze the validity of this phenomenon, the Pearson correlation between the harmonic ratio and the primary harmonic intensity was calculated, with and without a possible outlier value (FIG. 29). This low correlation demonstrates there is no statistically significant relationship between the amplitude of the signal the ultrasound is acquiring and the harmonic ratio between the primary and secondary signal components. This conclusion indicates that the ultrasound data acquisition is robust in terms of signal strength observed by the ultrasound probe.

Next the variation of harmonic ratio as it pertains to driving amplitude was analyzed. Using a driving frequency of 100 Hz, data was taken at an input acceleration of approximately 0.5, 1, and 1.5 g. Examining the correlation of the data to the physician scoring shows that as the amplitude of the driving vibration is increased, the correlation and statistical significance associated between the harmonic ratio and the physician scoring also increases, with the 1 g and 1.5 g data having significance at the 0.05 level (Table 7). Also incremented along with input amplitude is the $R^2$ value of pseudo-regression lines fitted to the scatter plot data (FIG. 30). Note that these lines are not true regression lines, due to the ordinal nature of the physician score data.

The variation of the harmonic ratio according to frequency of vibrational input was also examined. Three driving frequencies of 100 Hz, 150 Hz, and 200 Hz driven using the same amplifier gain setting (approximately 1 g at 100 Hz) were compared to the physician osteointegration score. Of the correlations between these data, only the 100 Hz data set was statistically significant, with the 200 Hz data having a higher P value and correlation than the 150 Hz data (Table 7). The $R^2$ value of pseudo regression lines fitted to the scatter plot data varied with frequency in a manner similar to the data correlations (FIG. 31). Again, note that these lines are not true regression lines, due to the ordinal nature of the physician score data.

To more accurately measure the osteointegration level inter-operatively, laser vibrometry was performed on the implants prior to extraction. The frequencies of the prominent spectrum peak were correlated to the physician score (Table 7). The laser data showed a statistical significant correlation to the physician score data, and a high $R^2$ value of the pseudo regression line fitted to the scatter plot data (FIG. 32). Again, this line is not a true regression line, due to the ordinal nature of the physician score data.

These studies indicate that patient characteristics of implant size, patient age, and gender did not statistically correlate to the physician scoring criteria for osteointegration. Other operative factors such as polywear, presence of cysts, and amount of time the device has been implanted also did not correlate statistically to the physician scoring criteria. In observing correlations not including the physician score variable, intuitive relationships such as polywear were positively correlated to implant time (Rho=0.661, p=0.003), and gender was positively correlated with implant size (male=larger size, Rho=0.678, p=0.002). A peripheral relationship between gender and implant time (male=longer time, Rho=0.472, p=0.048) was also observed.

In an attempt to quantify the intuition of the physician regarding talar looseness during the clinical examination, the physician's estimate of osteointegration fixation according to preoperative notes was correlated against the inter-operative score. The preoperative guess was significantly correlated with the inter-operative findings (Rho=0.567, p=0.018). However, a likelihood ratio analysis, which is a more robust test of significance with a dichotomous variable, failed to demonstrate the statistical significance of the physician's guess paired to the operative data (p=0.132).

Experience with the physician score data collection process raised the question of whether the physician scores of "1" and "2" might be difficult to distinguish between during data collection. Therefore, an analysis of the data correlations combining the "1" and "2" score into a four point physician score was performed, and the results are shown in Table 8 (below). Though the 100 Hz driving frequency ultrasound data's correlation improved, most other data remained constant, with an exception of implant size, which decreased slightly.

Ordinal Logistic Regression

Regression was used after the correlation analysis to more intricately define the relationship between metrics, as well as to develop a theoretical model to map the clinical and inter-operative data to the physician osteointegration score. Ordinal logistic regression is required due to the nature of the physician score variable.

For the first step in the ordinal logistic regression model, the full sample ultrasound data taken at 100 Hz driving frequency was used as the covariate to the physician score dependent variable. Using just this variable as a covariate, the model was fitted with a significance of P=0.035, but did not pass the parallel line test (Table 9). This indicates that a proportional odds ordinal logistic regression model (meaning same coefficients across all categories) is no better than a more complex general logistic regression model with different coefficients for each category. Also, the pseudo $R^2$ value of 0.19 depicts a poor model correlation with the data, and an analysis of the predicted physician scores versus the actual physician scores shows a relatively poor correlation that was not statistically significant.

TABLE 8

Spearman's Rho comparisons between physician's osteointegration score and test metrics from clinical testing, inter-operative testing, and patient characteristics.

| Physician's Osteointegration Score vs. | Spearman's Rho Coef. | Sig. (2-tailed) |
|---|---|---|
| Ultrasound 100 Hz Ratio (Primary) (n = 18) | −0.789 | 0.0001 |
| 1$^{st}$ Harmonic Amplitude (n = 18) | 0.161 | 0.523 |
| Ultrasound 100 Hz 1.5 g Ratio (n = 11) | −0.727 | 0.011 |
| Ultrasound 100 Hz 1 g Ratio (n = 11) | −0.670 | 0.024 |

TABLE 8-continued

Spearman's Rho comparisons between physician's osteointegration score and test metrics from clinical testing, inter-operative testing, and patient characteristics.

| Physician's Osteointegration Score vs. | Spearman's Rho Coef. | Sig. (2-tailed) |
|---|---|---|
| Ultrasound 100 Hz 0.5 g Ratio (n = 11) | −0.439 | 0.177 |
| Ultrasound 150 Hz Ratio (n = 18) | −0.302 | 0.223 |
| Ultrasound 200 Hz Ratio (n = 18) | −0.413 | 0.088 |
| Laser Peak Frequency (n = 11) | 0.916 | 0.00008 |
| Size (n = 18) | 0.334 | 0.176 |
| Age (n = 18) | −0.194 | 0.440 |
| Implant Time (n = 18) | 0.145 | 0.567 |
| Gender (n = 18) | 0.251 | 0.316 |
| Poly-wear (n = 17) | 0.279 | 0.261 |
| Presence of Cysts (n = 17) | −0.285 | 0.251 |
| Physician's Fixation Estimation (n = 17) | 0.570 | 0.017 |

TABLE 9

Various ordinal logistic regression models and the metrics for goodness-of-fit.

| Factors & Covariates (n = 18) | Model Statistics | | | Prediction Statistics | |
|---|---|---|---|---|---|
| | Model Sig. | Pseudo $R^2$ | Parallel Test Sig. | Spearman's Rho | Likelihood Ratio Sig. |
| Ultra 100 Hz | P = 0.035 | 0.231 | P = 0.0001 | 0.649 | P = 0.119 |
| Ultra 100 Hz, Size | P = 0.00018 | 0.782 | P = 0.413 | 0.815 | P = 0.001 |
| Ultra 100 Hz, Size, Gender | P = 0.00038 | 0.786 | P = 0.619 | 0.815 | P = 0.002 |
| Ultra 100 Hz, Size, Age | P = 0.000005 | 0.899 | P = 0.977 | 0.922 | P = 0.00002 |

To improve the model, patient characteristic data were incorporated into the model as co-factors. Implant size was chosen next due to its high correlation and low p value relative to the other patient data. Though implant size data were not shown to be significantly correlated itself, they can make a contribution to the model accuracy by incorporating more information to assist the fit of the more restrictive proportional odds model. The side effect was an increase in model complexity with more coefficients. The implant size data and the ultrasound data taken at 100 Hz driving frequency were now used to construct a regression (see Table 9, row 2). Using these variables as a factor and a covariate, the model was fitted with a significance of P=0.00018, and passed the parallel line test. The pseudo $R^2$ value of 0.782 now depicted a much better correlation with the data. An analysis of the predicted scores versus actual scores showed a better correlation that was statistically significant.

In an attempt to further improve the model, the next patient characteristic incorporated into the model was gender. Patient gender was chosen next due to its high correlation and lower p value relative to the other patient data. Although these data were not shown to be significantly correlated, the criteria can also make a contribution to the accuracy of the model, at the expense of model complexity. The patient gender, implant size data and the ultrasound data taken at 100 Hz driving frequency were now used to construct a regression (see Table 9, row 3). Using these variables as two factors and a covariate, the model was fitted with a significance of P=0.00038 and passed the parallel line test. The pseudo $R^2$ value of 0.786 again denotes no improvement of correlation with the data compared to the two variable model. An analysis of the predicted scores versus actual scores also showed the same correlation as before.

Because gender had little effect upon the model, patient age was the next characteristic incorporated into the model. The patient age, implant size data, and the ultrasound data taken at 100 Hz driving frequency were now used to construct a regression (Table 9, row 4). Using these variables as a factor and two covariates, the model was fitted with a significance of P=0.000005 and passed the parallel line test. The pseudo $R^2$ value of 0.899 denotes a significant improvement of correlation compared to the previous two and three variable models. An analysis of the predicted scores versus actual scores also showed a statistically stronger overall correlation compared to the previous models. A scatter plot of the predicted score data versus the actual score data can be seen in FIG. 33. The coefficients pertaining to the three models are shown in Table 10.

TABLE 10

Various ordinal logistic regression models and corresponding coefficients and intercepts.

| Factors and Covariates | $\theta_1$ | $\theta_2$ | $\theta_3$ | $\theta_4$ | U100 Hz | Size 2 | Size 3 | Size 4 | Size 5 | Sex | Age |
|---|---|---|---|---|---|---|---|---|---|---|---|
| Ultra 100 Hz | −5.74 | −2.51 | −0.19 | 0.47 | −284.2 | NA | NA | NA | NA | NA | NA |
| Ultra 100 Hz, Size | −29.6 | −25.5 | −5.14 | −1.41 | −16910 | −12.8 | 0.58 | 248 | 10.6 | NA | NA |
| 100 Hz, Size, Gndr | −26.7 | −22.3 | −4.47 | −0.95 | −14918 | −9.38 | 1.87 | 219 | 9.54 | −1.35 | NA |
| 100 Hz, Size, Age | −397 | −385 | −125 | −85.1 | −196322 | −211 | 4.92 | 2877 | 128 | NA | −1.02 |

TABLE 11

Ordinal logistic regression models using increased amplitude data and four point physician score data with the metrics for goodness-of-fit. Three-Category size variable combines sizes 3-4 and 5-6.

| Factors and Covariates (n = 11) | Model Statistics | | | Prediction Statistics | |
|---|---|---|---|---|---|
| | Model Sig. | Pseudo $R^2$ | Parallel Test Sig. | Spearman's Rho | Likelihood Ratio Sig. |
| Ultra 100 Hz 1.5 g | P = 0.001 | 0.646 | P = 0.74 | 0.822 | P = 0.018 |
| Ultra 100 Hz 1.5 g, Size | Quasi-Complete Separation. Did Not Converge. | | | | |
| Ultra 100 Hz 1.5 g, Age | P = 0.005 | 0.657 | P = 0.956 | 0.822 | P = 0.018 |
| (n = 18) | Dependent Variable Four Point Physician Score | | | | |
| Ultra 100 Hz | P = 0.0004 | 0.538 | P = 0.074 | 0.745 | P = 0.003 |
| Ultra 100 Hz, Size | P = 0.0004 | 0.763 | P = 0.376 | 0.800 | P = 0.002 |
| Ultra 100 Hz, Size, Age | P = 0.00004 | 0.870 | P = 0.835 | 0.901 | P = 0.00002 |

Previous correlation statistics suggested that an increase in driving frequency amplitude improved the correlation and the signal to noise ratio of the ultrasound data. Also, previous scatter plots, as well as experience from the collected data, suggest that the physician scores of "1" and "2" are difficult to distinguish and correlation may be strengthened by combining these categories together. To explore the effect of these two theories, the 100 Hz data set with the increased amplitude, and a four point physician score (combining scores 1 and 2) was used to construct regression models (Table 11).

Starting with the 1.5 g amplitude 100 Hz data as a covariate, the model was fitted with a significance of P=0.001 and passed the parallel line test. The pseudo $R^2$ value of 0.646 demonstrates a fair correlation with the data. An analysis of the predicted scores versus actual scores shows a good correlation that was statistically significant; however, it is worth noting that the lower sample number of the 1.5 g ultrasound data will conservatively bias this correlation, making it difficult to directly compare to the previous 1 g 100 Hz ultrasound data. Attempting to include the factor of implant size with a small sample size caused a separation in the data, which prevented the iterations from converging due to zero determinant values. Patient age was chosen next for incorporation, over gender, because of its greater effect according to the previous regular ultrasound data regressions; however, it did not appreciably increase the model fit for the increase in complexity it caused.

Using the four-point physician score as a dependent variable, the standard 100 Hz ultrasound data were fitted into a regression model again with a significance of P=0.0004 and also passed the parallel line test (Table 11). The pseudo $R^2$ value of 0.538 shows a more than two-fold improvement of correlation with the four-point data compared to the five-point physician score model. An analysis of the predicted scores versus actual scores also showed a higher correlation that was statistically significant compared to the five point model. In contrast, adding the implant size variable or implant size and age together in the regression, the model pseudo $R^2$ values, predicted correlations, and related P values did not exceed those found in the analogous versions of the five-point score model.

The ordinal logistic regression model was constructed using the laser peak frequency data as the covariate to the physician score dependent variable. Using this variable as a covariate, the model was fitted with a significance of P=0.00013 and passed the parallel line test (Table 12). The regression model for the laser data also produced a pseudo $R^2$ value of 0.789. Analysis of the predicted physician scores versus the actual physician scores for the laser data showed a strong correlation of 0.939 that was statistically significant.

TABLE 12

Laser data ordinal logistic regression model and the metrics for goodness-of-fit.

| Factors and Covariates (n = 11) | Model Statistics | | | Prediction Statistics | |
|---|---|---|---|---|---|
| | Model Sig. | Pseudo $R^2$ | Parallel Test Sig. | Spearman's Rho | Likelihood Ratio Sig. |
| Laser Peak Freq. | P = 0.00013 | 0.789 | P = 0.450 | 0.939 | P = 0.006 |

To determine the underlying function type that would best model the ultrasound and laser data, a curve was fit to each of the data sets versus the physician score data. Due to the fact that the physician score data are ordinal, these curve fits serve only as a starting point to determine the function that should be used to model the laser versus ultrasound data.

Because less laser data were available, the ultrasound data were down-sampled to equally correspond with the laser data. An exponential function, a logarithmic function, and a power function were fit to the ultrasound and laser data (Table 13). The best curve fitting function for both data sets was the exponential function, as shown in FIGS. 34 and 35.

$$F(x) = a * \exp^{\beta * x} \tag{14}$$

TABLE 13

Curve fit statistics for ultrasound and laser data.

| Fitted Data | Exponential $R^2$ | Logarithmic $R^2$ | Power $R^2$ |
|---|---|---|---|
| Ultrasound 100 Hz (n = 18) | 0.538 P = 0.010 | 0.371 P = 0.047 | 0.439 P = 0.026 |
| Laser Peak Freq. (n = 18) | 0.849 P = 0.00006 | 0.614 P = 0.004 | 0.776 P = 0.0003 |

Using the two suggestions for model functions given by the curve fitting statistics, the laser data and the ultrasound data were combined so that the laser data could be written as a function of the ultrasound data.

$$\text{Laser}(x) = a^* \exp^{b*x} \quad (15)$$

$$\text{Ultrasound}(x) = c^* \exp^{d*x}, \quad (16)$$

where the variable x represents the physician score.

By manipulating the ultrasound equation and combining it with the laser equation, one can determine the function type that relates the laser and ultrasound data together. First one solves the ultrasound equation for the physician score variable, represented here by x:

$$x = \frac{\ln\left(\frac{\text{Ultrasound}(x)}{c}\right)}{d}. \quad (17)$$

Then, Eq. (17) is inserted into the laser model equation, Eq. (15):

$$\text{Laser}(x) = a * \exp^{\frac{b*\ln\left(\frac{\text{Ultrasound}(x)}{c}\right)}{d}}. \quad (18)$$

Algebraic manipulation and combining constants together yields the following relationships:

$$\text{Laser} = \alpha * \text{Ultrasound}^{\beta} \quad (19)$$

$$\alpha = \frac{a}{c} \quad (20)$$

$$\beta = \frac{b}{d}.$$

Combining the two model functions together produces a power function to describe the relationship between the ultrasound and laser data. Although these curves assume a linear relation between points on the physician score, any irregularities present will cancel out when both model equations are combined. For example, if the physician scores actually increased exponentially, the assumption of linearity would give the relationship:

$$\text{Physician\_score\_linear} = l^* \ln(\text{Physican\_score\_exp}) + m \quad (21)$$

Substituting this relationship in both curves provides the following relationships:

$$\text{Laser}(x) = a * \exp^{\ln\left(\left(\frac{PSEXP}{m}\right)^{b*l}\right)} \quad (22)$$

$$\text{Ultrasound}(x) = c * \exp^{\ln\left(\left(\frac{PSEXP}{m}\right)^{d*l}\right)}. \quad (23)$$

Eqs. (22) and (23) can be simplified to:

$$\text{Laser}(x) = \frac{a}{m^{b*l}} * PSEXP^{b*l} \quad (24)$$

$$\text{Ultrasound}(x) = \frac{c}{m^{d*l}} * PSEXP^{d*l}. \quad (25)$$

Eqs. (24) and (25) can be combined to the same power form but with different constants to yield:

$$\text{Laser} = \alpha * \text{Ultrasound}^{\beta} \quad (26)$$

$$\alpha = \frac{a}{c^{b*d}} \quad (27)$$

$$\beta = \frac{b}{d}.$$

Computing the least squares linear regression on the linearized form of Eq. 27 produced the model given in Table 14.

TABLE 14

Linear regression statistics for the linearized ultrasound and laser data.

| Fitted Data (n = 11) | Correlation | $R^2$ | ANOVA | Intercept [$\ln(\alpha)$] | Slope $\beta$ |
|---|---|---|---|---|---|
| Laser-Ultrasound | 0.629 | 0.396 | P = 0.038 | 3.922 P = 0.016 | −0.408 P = 0.038 |
| Laser-Ultrasound (1.5 g) | 0.790 | 0.625 | P = 0.020 | 3.493 P = 0.024 | −0.568 P = 0.020 |

The model produced a relatively high correlation with a weaker $R^2$ value relating only about 40 percent of the variation in the dependent variable due to the independent variable. These values of variation in the model were shown by ANOVA to be statistically significant. To determine if the model would be strengthened using the higher amplitude ultrasound data due to suggestions in previous analyses of its decreased variability, the model was reconstructed using the linearized form of the 1.5 g ultrasound data (Table 14, row 2). This statistically significant model produced better correlation and explained variability ($R^2$) values. Plots with the regular and increased ultrasound versus laser data and associated regressions can be seen in FIGS. 36 and 37. FIG. 36 graphically illustrates a power function curve fit for laser frequency data versus a first set of ultrasound harmonic ratio data, while FIG. 37 graphically illustrates a power function curve fit for laser frequency data versus a second set of ultrasound harmonic ratio data.

Discussion of Empirical Studies

The goal of the empirical studies was to investigate the possibility of quantifying the osteointegration of an ankle prosthesis talar component non-invasively. This investigation was done using vibrometry methodology and a novel application of Doppler ultrasound. Validation of this technique was accomplished using physician grading criteria inter-operatively, as well as laser Doppler vibrometry before implant extraction.

The results show that the technique of ultrasound vibrometry is indicative of talar component osteointegration, as defined by the physician. This conclusion was shown at the outset through the presence of a significant correlation between the ultrasound data and the physician score. To make sure that some artifact of ultrasound data collection was not biasing the results, the correlation and scatter plot graph of the osteointegration harmonic ratio metric with respect to the amplitude of the ultrasound received signal was analyzed and found to be unrelated. To explore the sensitivity of the data and to determine optimal acquisition parameters, an analysis of driving amplitude and frequency was undertaken.

The increase in driving amplitude corresponded to an increase in the ultrasound data correlation with the physician score. The $R^2$ value of a pseudo regression line also increased in connection with increasing driving amplitudes. Since this value represents the percent of variation of the ultrasound data as explained by an increment in physician score, increasing values depict a favorable increase in the signal-to-noise ratio of the ultrasound data. These findings suggest that by increasing the driving vibration amplitude, the vibro-impact threshold of the talar component-bone system is surpassed, making its output vibration more sensitive to reduced osteointegration. This sensitivity increases the nonlinearities present in the system output vibration, which is acquired by the ultrasound.

Also investigated was the effect of driving frequency on the relationship between ultrasound data and physician score. Correlation data, statistical significance, and $R^2$ values were highest with 100 Hz data, yet were higher with 200 Hz data than 150 Hz data. Due to the strong effect driving amplitude had on the data, and the fact that amplitude output of the actuator was not constant with frequency, the actual output versus frequency was examined. After connecting an accelerometer to the electromagnetic actuator and ankle-foot orthosis, the accelerometer output was collected for a range of driving frequencies (FIG. 38). Due to the characteristics of this system, the actual output of the device fails to decrease monotonically, and instead, severely dips down around 150 Hz, increasing slightly again at 200 Hz. This result explains the improved correlation and $R^2$ values of the 200 Hz data over the 150 Hz data, and denotes the strong relationship the data exhibit regarding amplitude instead of frequency for this range of tested bandwidth.

Because of the subjective nature of the physician criteria score of osteointegration, a secondary quantitative measure of osteointegration that could be obtained inter-operatively was acquired. This measurement was acquired using laser Doppler and impulse testing to perform vibrometry directly on the component prior to extraction. For the limited data that were collected, the correlation, statistical significance, and $R^2$ value of a pseudo-curve fit measured against the physician score was found to correspond highly and with statistical significance. This finding is valuable, not only as a validation of the subjective physician score, but as a possible quantitative continuous variable metric to be related to the ultrasound data.

In connection with the acquisition of the ultrasound and laser data, various patient characteristics were identified to assist in regression modeling. In an analysis of the correlation between the patient characteristics and physician score, no metrics were found to be statistically correlated. Due to the possible slight effects of the patient characteristic data on osteointegration, the lack of statistical significance (particular in the implant size metric) might be due to lack of cases for statistical power. When compared against themselves, correlations such as polywear and gender were correlated with the time of device implantation as well as the intuitive male gender, and implant size correlation. The correlations related to male gender and time of implantation are interesting and may be due to osteopenic differences in the genders especially at this high age range.

As an exercise to determine the intuition of the physician regarding osteointegration during preoperative exams, physician's guess of fixation data was extracted from preoperative notes and correlated with the physician's osteointegration score, though the extracted guess from each patient was sometimes difficult to ascertain. These guess data were found to statistically correlate to the score data, although as a binary variable, this result is tenacious at best, for this number of samples. This result is depicted in the lack of significance between the variables when analyzed by a likelihood ratio chi-squared test, which means that the previous correlation might be biased by an outlier and would be sensitive to one or two changes in the data set.

Due to some irregularity seen in the ultrasound versus score data scatter plot around the scores "1" and "2", an investigation was undertaken to determine if combining these scores into a single category would provide better results. Although the basic 100 Hz ultrasound data improved slightly, the rest of the data remained the same, or in the case of implant size, decreased slightly. The difference between the qualitative scores of "1" and "2" on the physician scale is scant and is difficult to distinguish. A four-point scale might be better suited than a five-point scale; however, more data should be collected to establish this.

In order to create a usable model for predicting osteointegration that directly correlates the ultrasound data to the intuitive physician score, an ordinal logistic regression was compiled. This type of regression is required because of the ordinal nature of the physician score data. Using just the 100 Hz ultrasound data, the model was constructed with statistical significance, but it was not found to be an improvement on a general model, and its predicted scores were non-significant. By using implant size and patient age as other factors and covariates in the model, the regression was found to be sufficient and produced good predictions. Unfortunately these added factors increased the complexity of the model, and poorly correlated variables such as age can also decrease the model's ability to correctly predict separate data sets. Using the larger amplitude 100 Hz ultrasound data or the four-point scoring, however, produced regression models that output good, statistically significant predictions. This determination helped to achieve the goal of producing a model that directly predicts osteointegration as a result of clinical ultrasound testing.

To further validate the inter-operative laser vibrometry data, and to build a case for it to be used as a quantified metric of osteointegration, the laser data were modeled against the physician score with an ordinal logistic regression. The model developed could be constructed without using any covariates other than the laser data, and showed statistically significant goodness-of-fit, as well as producing highly correlated predictions. This methodology alone could be used to decide whether to extract particular parts of a prosthesis during a revision, or help in the gathering of quantified data for epidemiological purposes.

Finally, based on the previous statistical findings relating both the ultrasound and laser data to the physician score, a nonlinear and linear regression was investigated to acquire a powerful quantitative model linking the ultrasound data directly to the continuous laser data. Not only would this model be statistically more robust and easier to implement mathematically, but less subjective overall. By finding pseudo-regressions of exponential origin for both laser and ultrasound data versus the ordinal physician score, a power law model was algebraically derived to represent the relationship between the ultrasound and laser data directly. This derivation constituted an important analytical step, because assuming a power law relationship without a physical basis would be difficult to explain, since exponential functions are more common in biological and dynamic systems. Once the relation equation was derived, its form allowed for linearization and subsequent use in a standard ordinary least-squares linear regression algorithm. The coefficients to construct the model were found to be statistically significant for both the regular 100 Hz ultrasound data and the increased amplitude 100 Hz data, although the higher amplitude data displayed better fit and correlation.

Due to the complexity of the ankle joint, as well as the current design of total ankle replacement technology, the success rate of total ankle surgery is poor compared to other joint replacement procedures. Since it has been found that most revisions involve a loose talar component, and there is no modality for the determination of osteointegration clinically, the techniques disclosed herein can be beneficially employed to quantify osteointegration non-invasively, which is a substantial medically important benefit.

While the concepts disclosed herein are particularly well suited to evaluating the osteointegration of simulated ankle joints, it should be recognized that these concepts can be used to evaluate the osteointegration of other implants as well. As arthroplasty becomes increasing popular for a variety of joints, the ability to determine each device's integration becomes more and more important to a patient's well being and implant success. This methodology could be transferred to a variety of arthroplasty applications, such as hip, knee, shoulder, and the expanding fields of extremity arthroplasty and spine. Besides using this technique for evaluating hardware, it could also be implemented to determine the severity of a non-union in an arthrodesis or an osteotomy.

The inter-operative laser vibrometry technique can also be used to assist surgery. Determining if implant components have been properly press fit, measuring the rigidity of polyethylene bearings in capture mechanisms, and ascertaining the fit and fixation of plates and other hardware could be accomplished using this technique.

Not only can a novel device of the type disclosed above be manufactured and marketed for use in osteointegration identification, but an inexpensive facsimile could be constructed in many hospitals and clinics with materials at hand. This approach would provide some budget-care clinics with the resources to measure osteointegration and therefore suggest the appropriate treatment plan.

Finally in the context of the total ankle replacement, because this methodology is able to non-invasively quantify osteointegration, a tailored and more optimized approach to post-surgical rehabilitation can be devised. The optimized approach would be performed in weekly or monthly increments after the initial cast has been removed. The tracking of the fixation can not only be useful in dealing with non-compliant patients, but also as a quantified output of various rehabilitation techniques. This metric of fixation could also be used to track the efficacy of various surgical methods or products designed to increase osteointegration.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for quantitatively evaluating a degree of osteointegration of an orthopedic prosthesis in a patient, comprising the steps of:
   acquiring a calibrated osteointegration data set, the calibrated osteointegration data set being previously correlated to quantitative degrees of osteointegration of the orthopedic prosthesis to establish a baseline;
   non-invasively inducing vibrations in the patient proximate to the orthopedic prosthesis using an actuator for inducing vibration externally coupled to a skin of the patient;
   using an ultrasound transducer to non-invasively collect ultrasound data through the skin of the patient indicative of a degree of osteointegration of the orthopedic prosthesis in the patient;
   analyzing the ultrasound data to quantitatively evaluate the degree of osteointegration of the orthopedic prosthesis in the patient by, at least:
      taking Fourier transforms of the ultrasound data,
      determining a magnitude ratio of a second harmonic component of the ultrasound data to a driving frequency of the vibrations from the Fourier transforms,
      comparing the magnitude ratio to the calibrated osteointegration data set, and
      determining a quantitative score of orthopedic prosthesis osteointegration based at least in part on the comparing; and
   outputting the quantitative score of orthopedic prosthesis osteointegration to a user.

2. The method of claim 1, wherein the calibrated osteointegration data set has been previously correlated to degrees of osteointegration as measured inter-operatively using laser vibrometry.

3. The method of claim 1, wherein the calibrated osteointegration data set has been previously correlated to degrees of osteointegration as determined by a medical practitioner during an invasive examination of a corresponding orthopedic prosthesis.

4. The method of claim 1, wherein the actuator for inducing vibration comprises an electromagnetic actuator.

5. The method of claim 1, wherein the orthopedic prosthesis comprises an artificial ankle joint and the method further comprises the step of positioning an ankle of the patient in a plantar flexion configuration, to rotate a talar component toward an anterior of the ankle of the patient, before inducing the vibrations.

6. The method of claim 1, wherein the orthopedic prosthesis comprises an artificial ankle joint and the method further comprises the step of isolating a foot of the patient that includes the artificial ankle joint from other vibration sources before inducing the vibrations.

7. The method of claim 1, wherein the step of using ultrasound to noninvasively collect data indicative of the degree of osteointegration of the orthopedic prosthesis comprises the step of avoiding contact between a vibration source used to induce the vibrations and an ultrasound probe used to collect the data.

8. The method of claim 1, wherein the step of using ultrasound to noninvasively collect data indicative of the degree of osteointegration of the orthopedic prosthesis comprises the step of securing an ultrasound probe used to collect the ultrasound data in a fixed position before inducing the vibrations and collecting the ultrasound data.

9. The method of claim 1, wherein the step of non-invasively inducing vibrations in the patient proximate to the orthopedic prosthesis comprises the step of inducing vibrations at a frequency within a range from 80 Hz to 500 Hz.

10. The method of claim 1, wherein using the ultrasound transducer to non-invasively collect ultrasound data through the skin of the patient indicative of the degree of osteointegration of the orthopedic prosthesis in the patient comprises moving a gate depth of the ultrasound transducer off a surface of the orthopedic implant.

11. A system for quantitatively evaluating a degree of osteointegration of an orthopedic prosthesis in a patient, comprising:
an actuator for inducing vibration for externally coupling to a skin of the patient and for non-invasively inducing vibrations in the patient proximate to the orthopedic prosthesis;
an ultrasound probe to non-invasively collect patient ultrasound data through the skin of the patient indicative of the degree of osteointegration of the orthopedic prosthesis;
a storage device including an osteointegration calibration data set that has been previously correlated to degrees of osteointegration to establish a baseline and has been acquired prior to collection of the patient ultrasound data; and
a processing circuit programmed to analyze the ultrasound data to quantitatively evaluate the degree of osteointegration of the orthopedic prosthesis in the patient by, at least:
taking Fourier transforms of the ultrasound data,
determining a magnitude ratio of a second harmonic component of the ultrasound data to a driving frequency of the vibrations from the Fourier transforms,
comparing the magnitude ratio to the osteointegration calibration data set,
determining a quantitative score of orthopedic prosthesis osteointegration based at least in part on the comparing, and
outputting the quantitative score to a user.

12. The system of claim 11, wherein the actuator for inducing vibration is able to generate vibrations at a frequency at least in a range from 80 Hz to 500 Hz.

13. The system of claim 11, wherein the osteointegration calibration data set has been previously correlated to degrees of osteointegration as measured inter-operatively using laser vibrometry.

14. The system of claim 11, wherein the osteointegration calibration data set has been previously correlated to degrees of osteointegration as determined by a medical practitioner during an invasive examination of a corresponding orthopedic prosthesis.

15. A method for quantitatively evaluating a degree of attachment between an orthopedic prosthesis and a patient's skeletal structure, whereby a calibrated attachment data set has been collected, the calibrated attachment data set having been previously correlated to degrees of attachment to establish a baseline, comprising the steps of:
inducing vibrations in at least one element selected from a group consisting of the patient's skeletal structure proximate to the orthopedic prosthesis and the orthopedic prosthesis using an actuator for inducing vibration that is externally coupled to the patient;
collecting data indicative of the degree of attachment between the orthopedic prosthesis and the patient's skeletal structure using at least one technique selected from a group consisting of laser vibrometry and ultrasound vibrometry;
analyzing the collected data indicative of the degree of attachment to quantitatively evaluate the degree of attachment between the orthopedic prosthesis and the patient's skeletal structure by, at least:
taking Fourier transforms of the collected data,
determining a magnitude ratio of a second harmonic component of the collected data to a driving frequency of the induced vibrations from the Fourier transforms,
comparing the magnitude ratio to the calibrated attachment data, and
determining a quantitative score of orthopedic prosthesis attachment based at least in part on the comparing; and
outputting the quantitative score of orthopedic prosthesis attachment to a user.

16. The method of claim 15, wherein the calibrated attachment data set has been previously correlated to indicate a degree of attachment by a medical practitioner during an invasive examination of a corresponding orthopedic prosthesis.

17. The method of claim 15, wherein the data indicative of the degree of attachment are collected using ultrasound vibrometry, and wherein the actuator for inducing vibration comprises an electromagnetic actuator.

18. The method of claim 15, wherein the data indicative of the degree of attachment are collected using laser vibrometry, and wherein the step of inducing vibrations comprises the step of repeatedly striking the orthopedic prosthesis during an operative procedure that exposes the orthopedic prosthesis.

19. The method of claim 15, wherein the data indicative of the degree of attachment are collected using laser vibrometry, and the method further comprises the steps of:
before inducing vibrations:
attaching a reflective component to the orthopedic prosthesis; and
focusing a laser vibrometer on the reflective component for collecting the data.

20. A system for quantitatively evaluating a degree of attachment between an orthopedic prosthesis and a patient's skeletal structure, comprising:
an actuator for inducing vibration for externally coupling to a skin of the patient and for inducing vibrations in at least one element selected from a group consisting of a patient's skeletal structure proximate to the orthopedic prosthesis and the orthopedic prosthesis;
a probe for collecting data indicative of the degree of attachment between the orthopedic prosthesis and the patient's skeletal structure, the probe being selected from a group consisting of a laser vibrometer and an ultrasound probe;
a storage device including an attachment calibration data set that has been previously correlated to degrees of attachment to establish a baseline and has been acquired prior to collection of the data indicative of the degree of attachment between the orthopedic prosthesis and the patient's skeletal structure; and
a processing circuit that analyzes the data collected to quantitatively evaluate the degree of attachment between the orthopedic prosthesis and the patient's skeletal structure by, at least:
taking Fourier transforms of the collected data, determining a magnitude ratio of a second harmonic component of the collected data to a driving frequency of the induced vibrations from the Fourier transforms, comparing the magnitude ratio to the calibrated attachment data, and determining a quantitative score of orthopedic prosthesis attachment based at least in part on the comparing, and outputting the quantitative score of orthopedic prosthesis attachment based on the analysis of the data collected.

21. The system of claim 20, wherein the actuator for inducing vibration further comprises an impactor made from material selected from the group consisting of acrylic and polycarbonate and being operable to deliver a repeatable strike to the orthopedic prosthesis in vivo during an operative procedure that exposes the orthopedic prosthesis.

22. The system of claim 20, wherein the actuator for inducing vibration comprises an electromagnetic actuator operable at a frequency ranging from 80 Hz to 500 Hz.

23. The system of claim 20, further comprising a reflective component to be attached to the orthopedic prosthesis to facilitate the collection of data using the laser vibrometer.

* * * * *